(12) United States Patent
Garg et al.

(10) Patent No.: US 11,259,767 B2
(45) Date of Patent: Mar. 1, 2022

(54) SYSTEMS AND METHODS FOR ENHANCED DIAGNOSIS OF TRANSTHYRETIN CARDIAC AMYLOIDOSIS

(71) Applicant: Mayo Foundation for Medical Education and Research, Rochester, MN (US)

(72) Inventors: Ishan Garg, Chicago, IL (US); Andrew C. Hoffman, Rochester, MN (US); Geoffrey B. Johnson, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 544 days.

(21) Appl. No.: 16/359,729

(22) Filed: Mar. 20, 2019

(65) Prior Publication Data
US 2019/0290232 A1    Sep. 26, 2019

Related U.S. Application Data

(60) Provisional application No. 62/645,719, filed on Mar. 20, 2018.

(51) Int. Cl.
*A61B 6/00* (2006.01)
*A61B 6/03* (2006.01)
*A61K 51/02* (2006.01)

(52) U.S. Cl.
CPC ............. *A61B 6/503* (2013.01); *A61B 6/032* (2013.01); *A61B 6/037* (2013.01); *A61B 6/463* (2013.01); *A61B 6/469* (2013.01); *A61B 6/5235* (2013.01); *A61K 51/025* (2013.01)

(58) Field of Classification Search
CPC .......... A61B 6/503; A61B 6/032; A61B 6/037
See application file for complete search history.

(56) References Cited

PUBLICATIONS

Scully PR, et al. Prevalence of Cardiac Amyloidosis in Patients Referred for Transcatheter Aortic Valve Replacement. J Am Coll Cardiol. 2018;71(4):463-464.
Selvanayagam JB, et al. Evaluation and management of the cardiac amyloidosis. Journal of the American College of Cardiology. 2007;50:2101-10.
Siddiqi OK, et al. Cardiac amyloidosis: An update on pathophysiology, diagnosis, and treatment. Trends Cardiovasc Med. 2018;28(1):10-21.

(Continued)

*Primary Examiner* — Joseph M Santos Rodriguez
(74) *Attorney, Agent, or Firm* — Quarles & Brady LLP

(57) ABSTRACT

Systems and methods for enhanced diagnosis of transthyretin-related cardiac amyloidosis in a subject are disclosed. The systems and methods may use both SPECT imaging data as well as an anatomical imaging data, such as computed tomography (CT) data, to produce a combined image. Within the combined image, the radiotracer uptake between two volumes of interests are compared, one of which may represent the left ventricle of the subject and the other may represent the blood pool retention of the subject. Combining the anatomical imaging data with SPECT data enables better anatomical delineation and helps in avoiding areas with coronary or lymph node calcifications and overlying soft tissue and bony pathologies.

34 Claims, 11 Drawing Sheets
(6 of 11 Drawing Sheet(s) Filed in Color)

(56) References Cited

PUBLICATIONS

Sperry BW, et al. Non-cardiac uptake of technetium-99m pyrophosphate in transthyretin cardiac amyloidosis. J Nucl Cardiol. 2018.

Stats MA, et al. Varying levels of small microcalcifications and macrophages in ATTR and AL cardiac amyloidosis: implications for utilizing nuclear medicine studies to subtype amyloidosis. Cardiovascular Pathology. 2016;25:413-7.

Takezaki M, et al. Noninvasive diagnosis of cardiac involvement by technetium-99m-pyrophopahte(Tc-99m PYP) myocardial scintiography in 2 case with familial amyloid polyneuropathy and 1 case with secondary amyloidosis. Kaku Igaaku. 1989,26:1537-43. (English Abstract at end of document).

Tamaki S, et al. Emission computed tomography with technetium-99m pyrophosphate for delineating location and size of acute myocardial infarction in man. Br Heart J. 1984;52(1):30-37.

Trivieri MG, et al. (18)F-Sodium Fluoride PET/MR for the Assessment of Cardiac Amyloidosis. J Am Coll Cardiol. 2016;68(24):2712-2714.

Van Der Gucht A, et al. Apical sparing pattern of left ventricular myocardial (99m)Tc-HMDP uptake in patients with transthyretin cardiac amyloidosis. J Nucl Cardiol. 2017.

Vrana JA, et al. Classification of amyloidosis by laser microdissection and mass spectrometry-based proteomic analysis in clinical biopsy specimens. Blood. 2009;114:4957-9.

Wiltshire JP, et al. Lumbar muscle rhabdomylolysis as a cuase of acute reanl failure after Roux-en Y gastric bypass. Obesity Surgery. 2003;13:306-13.

Yamamato Y, et al. Novel insight for quantitative evaluation of cardiac amyloidosis using 201TICl and 99mTc-PYP SPECT. Annals of Nuclear Medicine. 2012;26:634-43.

Yilmaz A, et al. Comparative evaluation of left and right ventricular endomyocardial biopsy: differences in complication rate and diagnostic performance Circulation. 2010;122(9):900-909.

Murtagh B, et al. Electrocardiographic findings in primary systemic amyloidosis and biopsy-proven cardiac involvement. American Journal of Cardiology. 2005;95:535-7.

Bokhari, Sabahat, et al. "Standardization of 99m Technetium pyrophosphate imaging methodology to diagnose TTR cardiac amyloidosis." Journal of nuclear cardiology 25.1 (2018): 181-190.

Bourogianni, O., et al. "Isolated cardiac amyloidosis. Utility of bone seeking tracers scintigraphy in differentiating the subtype of amyloid: A case report." Journal of Nuclear Cardiology(2018): 1-5.

Castano, Adam, et al. "Serial scanning with technetium pyrophosphate (99m Tc-PYP) in advanced ATTR cardiac amyloidosis" Journal of Nuclear Cardiology 23.6 (2016): 1355-1363.

Ahmad MM, et al. The complementary nature of tissue Doppler to (99m)Tc-PYP imaging in diagnosis of right ventricular cardiac amyloidosis. J Nucl Cardiol. 2017.

Bennani SY, et al. Pilot study for left ventricular imaging phenotype of patients over 65 years old with heart failure and preserved ejection fraction: the high prevalence of amyloid cardiomyopathy. International Journal Cardiovascular Imaging. 2016;32:1403-13.

Bokhari S, et al. 99mTc-pyrophosphate scintigraphy for differentiating light-chain cardiac amyloidosis from the transthyretin-related familial and senile cardiac amyloidoses. Circ Cardiovasc Imaging. 2013;6:195-201.

Cappelli F, et al. Accuracy of 99mTc-Hydroxymethylene diphosphonate scintigraphy for diagnosis of transthyretin cardiac amyloidosis. J Nucl Cardiol. 2017.

Castano A, et al. Multicenter Study of Planar Technetium 99m Pyrophosphate Cardiac Imaging: Predicting Survival for Patients With ATTR Cardiac Amyloidosis. JAMA Cardiol. 2016;1:880-89.

Castano A, et al. Unveiling transthyretin cardiac amyloidosis and its predictors among elderly patients with severe aortic stenosis undergoing transcatheter aortic valve replacement. Eur Heart J. 2017;38(38):2879-2887.

Chang ICY, et al. Hydroxychloroquine-Mediated Cardiotoxicity With a False-Positive (99m)Technetium-Labeled Pyrophosphate Scan for Transthyretin-Related Cardiac Amyloidosis. Circ Cardiovasc Imaging. 2018;11(1).

Chen W, et al. Molecular imaging of amyloidosis: Will the heart be the next target after the brain? Curr Cardiol Rep. 2012;14:226-33.

Cheng Z, et al. Utility of combined indexes of electrocardiography and echocardiography in the diagnosis of biopsy proven primary cardiac amyloidosis. Annals of Noninvasive Electrocardiology. 2011;16:25-9.

Cooper LT, et al. The role of endomyocardial biopsy in the management of cardiovascular disease: a scientific statement from the American Heart Association, the American College of Cardiology, and the European Society of Cardiology Endorsed by the Heart Failure Society of America and the Heart Failure Association of the European Society of Cardiology. J Am Coll Cardiol. 2007;50(19):1914-1931.

Dewanjee MK, et al. Mechanism of localization of 99mTc-labeled pyrophosphate and tetracycline in infarcted myocardium. Journal of Nuclear Medicine. 1976;17:639-46.

Dharmarajan KK, et al. Transthyretin cardiac amyloidoses in older North Americans. J Am Geriatr Soc. 2012;60:765-74.

Di Bella G, et al. The mosaic of the cardiac amyloidosis diagnosis: role of imaging in subtypes and stages of the disease Eur Heart J Cardiovasc Imaging. 2014;15(12):1307-1315.

Dungu JN, et al. CMR-based differentiation of AL and ATTR amyloidosis. JACC Cardiovascular Imaging. 2014;7:133-42.

Eriksson P, et al. Non-invasive assessment of the presence and severity of cardiac amyloidosis: A study in familial amyloidosis with polyneuropathy by cross sectional echocardiography and technetium-99 m pyrophosphate scintigraphy. Br Heart J. 1984;52:321-6.

Falk RH, et al. Sensitivity of technetium-99m-pyrophosphate scintigraphy in diagnosing cardiac amyloidosis. Am J Cardiol. 1983;51:826-30.

Fontana M, et al. Prognostic value of late gadolinium enhancement cardiovascular magnetic resonance in cardiac amyloidosis. Circulation. 2015;132:1570-9.

Garcia-Gonzalez P, et al. Cardiac Amyloidosis Detected Using (18)F-florbetapir PET/CT. Rev Esp Cardiol (Engl Ed). 2016;69(12):1215.

Gertz MA, et al. Diagnosis, Prognosis, and Therapy of Transthyretin Amyloidosis. J Am Coll Cardiol. 2015;66(21):2451-2466.

Gertz MA, et al. Pathophysiology and treatment of cardiac amyloidosis. Nature Reviews Cardiology. 2015;12:91-102.

Gertz MA, et al. Utility of technetium Tc 99m pyrophosphate bone scanning in cardiac amyloidosis. Arch Intern Med. 1987;147:1039-44.

Gillmore JD, et al. Nonbiopsy Diagnosis of Cardiac Transthyretin Amyloidosis. Circulation. 2016;133:2404-12.

Gonzalez LE, et al. Wild-type transthyretin amyloidosis as a cause of heart failure with preserved ejection fraction. European heart Journal. 2015;36:2585-94.

Grogan M, et al. Natural History of Wild-Type Transthyretin Cardiac Amyloidosis and Risk Stratification Using a Novel Staging System. J Am Coll Cardiol. 2016;68(10):1014-1020.

Harb SC, et al. National patterns in imaging utilization for diagnosis of cardiac amyloidosis: A focus on Tc99m-pyrophosphate scintigraphy. J Nucl Cardiol. 2017;24(3):1094-1097.

Hutt DF, et al. Utility and limitations of 3,3-diphosphono-1,2-propanodicarboxylic acid scintigraphy in systemic amyloidosis. Eur Heart J Cardiovasc Imaging. 2014;15(11):1289-1298.

Kakhki VD, et al. Age-related normal variants of sternal uptake on bone scintigraphy. Clin Nucl Med. 2006;31(2):63-67.

Kollikowski AM, et al. In vivo quantification of amyloid burden in TTR-related cardiac amyloidosis. Intractable Rare Dis Res. 2017;6(4):291-294.

Koyama J, et al. Echocardiographic assessment of cardiac amyloidoses. Circulation Journal. 2015;79:721-34.

Lee SP, et al. 11C-Pittsburgh B PET imaging in cardiac amyloidosis. JACC Cardiovasc Imaging. 2015;8(1):50-59.

(56) References Cited

PUBLICATIONS

Lee VW, et al. Amyloidosis of heart and liver: comparison of Tc-99 m pyrophosphate and Tc-99 m methylene diphosphonate for detection Radiology. 1983;148:239-42.

Maleszewski JJ, et al. Relationship between monoclonal gammopathy and cardiac amyloid type. Cardiovascular Pathology. 2013;22:189-94.

Maleszewski JJ. Cardiac amyloidosis: pathology, nomenclature, and typing. Cardiovascular Pathology. 2015;24:343-50.

Mohammed SF, et al. Left ventricular amyloid deposition in patients with heart failure and preserved ejection fraction. JACC Heart Failure. 2014;2:113-22.

Mollee P, et al. How to diagnose amyloidosis. Intern Med J. 2014;44:7-17.

Moore PT, et al. The Utility of 99mTC-DPD Scintigrpahy in the Diagnosis of Cardiac Amyloidosis: An Australian Experience. Heart, Lung and Circulation. 2017. Advance online publication, doi: http://dx.doi.org/10.1016/j.hlc.2016.12.017.

Nakagawa M, et al. High prevalence of ATTR amyloidosis in endomyocardial biopsy-proven cardiac amyloidosis patients. Amyloid. 2013;20:138-40.

Narotsky DL, et al. Wild-Type Transthyretin Cardiac Amyloidosis: Novel Insights From Advanced Imaging. Can J Cardiol. 2016;32(9):1166 e1161-1166 e1110.

Osborne DR, et al. A Routine PET/CT Protocol with Streamlined Calculations for Assessing Cardiac Amyloidosis Using (18)F-Florbetapir. Front Cardiovasc Med. 2015;2:23.

Paueksakon P, et al. Leukocyte chemotactic factor 2 amyloidosis cannot be reliably diagnosed by immunohistochemical staining. Hum. Pathol. 2014;45:1445-50.

Pepys MB, et al. Binding of serum amyloid p-component (SAP) by amyloid fibrils. Clin Exp Immunol. 1979;38:284-93.

Perguini E, et al. Noninvasive etiologic diagnosis of cardiac amyloidosis using 99mTc-3,3-diphophono-1,2-propanodicarboxylic acid scintigraphy. Journal of the American College of Cardiology. 2005;46:1076-84.

Pinney JH, et al. Senile systemic amyloidosis: clinical features at presentation and outcome. Journal of the American Heart Association. 2013;2(2):e000098.

Pomerance A, et al. Experience with the sodium sulphate-Alcian Blue stain for amyloid in cardiac pathology. J Clin Pathol. 1976;29:22-6.

Quarta CC, et al. Longitudnal strain imaging in light-chain cardiac amyloidosis:can it help to refine the approach to treatment? Journal of the American College of Cardiology. 2012:60:1077-8.

Quarta CC, et al. High 99mTc-DPD myocardial uptake in a patient with apolipoprotein AI-related amyloidotic cardiomyopathy. Amyloid. 2013;20:48-51.

Rapezzi C, et al. Cardiac amyloidosis: the great pretender. Heart Fail Rev. 2015;20(2):117-124.

Rapezzi C, et al. Systemic cardiac amyloidoses: disease profiles and clinical courses of the 3 main types. Circulation. 2009;120:1203-12.

Rapezzi C, et al. Role of (99m)Tc-DPD scintigraphy in diagnosis and prognosis of hereditary transthyretin-related cardiac amyloidosis. JACC Cardiovasc Imaging 2011,4:659-70.

Rapezzi C, et al. Usefulness and limitations of 99mTc-3,3-diphosphono-1,2-propanodicarboxylic acid scintigraphy in the aetiological diagnosis of amyloidotic cardiomyopathy. Eur J Nucl Med Mol Imaging. 2011;38:470-8.

SYSTEMS AND METHODS FOR ENHANCED DIAGNOSIS OF TRANSTHYRETIN CARDIAC AMYLOIDOSIS

CROSS-REFERENCE TO RELATED APPLICATIONS

The present application claims priority from and benefit of U.S. Provisional Patent Application No. 62/645,719 filed on Mar. 20, 2018 and titled "Systems and Methods for Enhanced Diagnosis of Transthyretin Cardiac Amyloidosis". The entire disclosure of the above-identified provisional application is incorporated by reference herein.

STATEMENT REGARDING FEDERALLY SPONSORED RESEARCH

Not applicable.

BACKGROUND OF THE INVENTION

Cardiac amyloidosis (CA) is a progressive and fatal cause of heart failure with preserved ejection fraction (HFpEF) that has been grossly underdiagnosed [Ref. 1-4]. In one study, 17% patients with HFpEF who had no ante-mortem suspicion of CA were found to have CA at autopsy [Ref. 3]. A high prevalence (13.9 to 16%) of occult cardiac transthyretin related amyloid (ATTR) has also been noted in patients with aortic stenosis undergoing transcatheter aortic valve replacement (TAVR) [Ref. 5,6]. Amyloidosis is caused by a progressive extracellular deposition of insoluble fibrils that are composed of variety of serum proteins, leading to tissue destruction and organ function impairment [Ref. 7]. Amyloid is classified based on the protein that led to its deposition [Ref. 8]. The two most common types of cardiac amyloid that can cause heart failure are light chain amyloid (AL) and ATTR [Ref. 9-12]. It is essential to differentiate between these two types of amyloid as they are managed differently [Ref. 11,13,14]. The current gold standard for diagnosis of CA is endomyocardial biopsy (EMB) followed by mass spectrometry for amyloid subtyping on the biopsied tissue [Ref. 15,16]. Immunohistochemistry is also used for amyloid subtyping, with variable reliability [Ref. 15,17]. EMB is an invasive procedure and can lead to complications such as myocardial perforation, arrhythmias, pneumothorax and pulmonary embolization. The reported rate of complications ranges from less than 1 to 6 percent [Ref. 18,19]. In addition, these methods require significant expertise for both the vascular interventional procedure and the pathologic interpretation, which are not widely available. Therefore, there has been an unmet need for alternative non-invasive methods for diagnosing and differentiating between different types of cardiac amyloidosis. Noninvasive procedures like magnetic resonance imaging (MRI) and echocardiography can be helpful in differentiating restrictive cardiomyopathy caused by amyloid deposition from other types of cardiomyopathy, but neither imaging method can reliably differentiate between amyloid types [Ref. 20-26].

It has been known that cardiac amyloidosis can be detected by planar scintigraphy using bone seeking radiotracers like $^{99m}$Tc-3,3-diphophono-1,2-propanodicarboxylic acid (DPD), $^{99m}$Tc-methylene diphosphonate (MPD), and $^{99m}$Tc-pyrophosphate (PYP). However, these studies failed to recognize the need to differentiate ATTR from AL, and therefore concluded there was low sensitivity for detection of CA. Hence, its clinical use was not further studied [Ref. 27-30]. But with recent understanding that these radiotracers are highly sensitive and specific for ATTR CA [Ref. 31-34], there has been a reemergence in the interest for non-invasive diagnosis and differentiation of different types of cardiac amyloid. The currently used 2-D planar scintigraphy based heart to contralateral (HCL) ratio has shown an excellent diagnostic accuracy for detecting ATTR-CA. However, planar images have potential diagnostic limitations particularly in patients with bone pathologies, recent thoracic surgeries, myocardial infarction, cardiac trauma, renal failure and altered thoracic anatomy, which may lead to thoracic uptake of PYP unrelated to cardiac amyloid.

An alternative option to 2-D scintigraphy that has been recently studied has been to use SPECT/CT. In a recent study by Moore et al., $^{99m}$Tc-DPD SPECT/CT was used for assessment of cardiac amyloidosis in 21 subjects with heart failure due to amyloid (8 AL and 13 ATTR) [Ref. 39]. In that study a semi-quantitative visual scoring of cardiac retention was evaluated in accordance with criteria proposed by Perugini et al. [Ref. 40]. The results of the study showed a 100% sensitivity (Sn) but only 75% specificity (Sp) for detection of ATTR-CA. Similar results were observed in this study with quantitative comparison of cardiac retention relative to bone retention (sternum) (Sn=94.1% and Sp=80%). Comparison of the cardiac radiotracer retention relative to bone retention was used in this study and is a standard technique.

In a different study, Yamamoto et al. [Ref. 41] described a quantitative method, the PYP score, based on SPECT alone. It was defined as the ratio of myocardial mean counts to ventricular cavity mean counts and was used to assess the utility of $^{99m}$Tc-PYP for evaluation for cardiac amyloidosis in 13 subjects with heart failure due to amyloid (1 AL, 3 ATTRm, and 8 ATTRwt) and 37 subjects with heart failure attributable to non-amyloid causes. The PYP score was found to have a Sn of 84.6% and Sp of 94.5% for differentiating cardiac amyloidosis from non-amyloid causes of heart failure.

What is needed therefore is an improved system and method for enhanced diagnosis of transthyretin-related cardiac amyloidosis in a subject.

SUMMARY OF THE INVENTION

The present disclosure overcomes the aforementioned shortcomings by providing systems and methods for enhanced diagnosis of transthyretin-related cardiac amyloidosis in a subject. The systems and methods use both SPECT imaging data as well as an anatomical imaging data, such as computed tomography (CT) data, to produce a combined image. Within the combined image, the radiotracer uptake between two volumes of interests are compared, one of which may represent the left ventricle of the subject and the other may represent the blood pool retention of the subject. Combining the anatomical imaging data with SPECT data enables better anatomical delineation and helps in avoiding areas with coronary or lymph node calcifications and overlying soft tissue and bony pathologies. Previous diagnostic systems have struggled to avoid such troublesome areas, which can often be missed without anatomical information that helps to provide better visual evaluation of cardiac radiotracer uptake. Further, because the comparison of the uptake may be made with the blood pool of the subject, patients with abnormal bone calcifications can still be accurately diagnosed. The culmination of these novel features allowed a diagnostic study using the methods and systems described herein to produce 100% Sp and 100% Sn results.

In one aspect, the present disclosure provides a method for diagnosing transthyretin cardiac amyloidosis in a subject. The method can comprise introducing a technetium-99m pyrophosphate radiotracer into a subject; acquiring single-photon emission computed tomography (SPECT) image data of a cardiac region of the subject based on the uptake of the radiotracer; acquiring anatomical image data of the cardiac region of the subject; combining the SPECT image data and the anatomical image data to produce a combined three-dimensional image of the cardiac region; and comparing the radiotracer uptake present within a first volume of interest and a second volume of interest, wherein both volumes of interest are located within the combined image of the cardiac region.

In another aspect, the present disclosure provides a method for diagnosing transthyretin cardiac amyloidosis in a subject. The method can comprise introducing a radiotracer into a subject; acquiring single-photon emission computed tomography (SPECT) image data of a cardiac region of the subject based on the uptake of the radiotracer; acquiring anatomical image data of the cardiac region of the subject; combining the SPECT image data and the anatomical image data to produce a combined three-dimensional image of the cardiac region; and comparing the radiotracer uptake present within a first volume of interest and a second volume of interest, wherein the first volume of interest is representative of the left ventricle of the subject and the second volume of interest is representative of the blood pool of the subject.

In yet another aspect, the present disclosure provides a system for diagnosing transthyretin cardiac amyloidosis in a subject. The system can comprise a source of technetium-99m pyrophosphate radiotracer; means for introducing the technetium-99m pyrophosphate radiotracer into a subject; a single-photon emission computed tomography (SPECT) system configured to acquire SPECT image data of a cardiac region of the subject based on the uptake of the radiotracer; an imaging system configured to acquire anatomical image data of the cardiac region of the subject; a processor configured to combine the SPECT image data and the anatomical image data to produce a combined three-dimensional image of the cardiac region and compare the radiotracer uptake present within a first volume of interest and a second volume of interest, wherein both volumes of interest are located within the combined image of the cardiac region.

Various other features of the present invention will be made apparent from the following detailed description, claims, and the drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EXEMPLARY EMBODIMENTS

Figure 1:
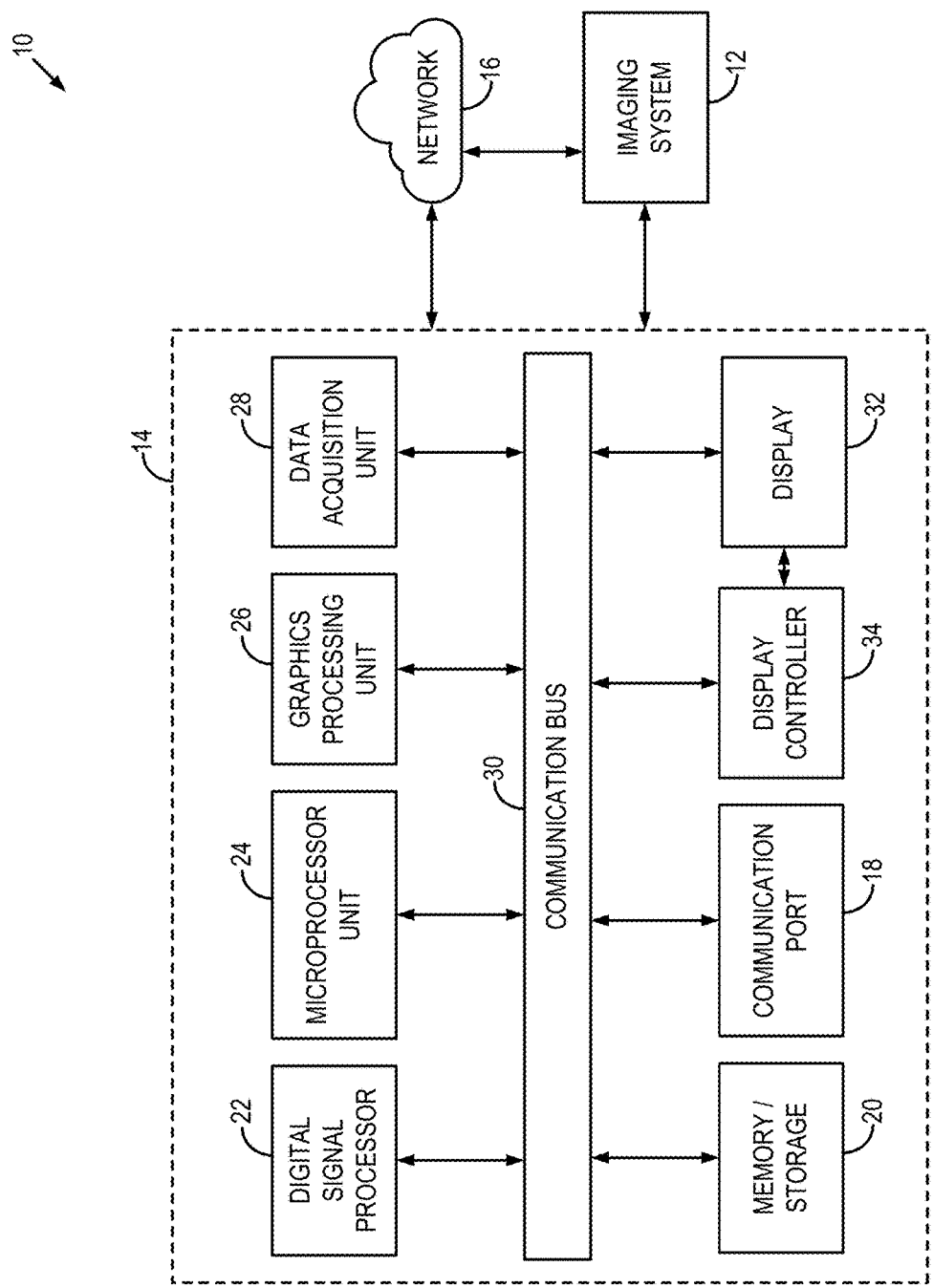
FIG. 1 is a schematic diagram of an example computer system that can be configured to implement the systems and method of the present disclosure.

As will be described, the present disclosure provides systems and methods for enhanced diagnosis of transthyretin-related cardiac amyloidosis using $^{99m}$Tc pyrophosphate imaging. The diagnostic technique used herein, occasionally referred to as the "3D-PYP score", is capable of producing higher selectivity and specificity results when compared to traditional methods, such as planar scintigraphy.

As used herein, volume of interest (VOI) may be defined as a distinct volume within a subject that can be representative of a specific anatomical region or part of the subject. The volume of interest may comprise the entire anatomical region or only a portion of the anatomical region. The volume of interest is often described as being represented by a smaller volume or dataset contained within a larger three dimensional (3D) image or dataset. The volume of interest may be any suitable shape capable of representing the specific anatomical region. Further, the shape of the volume of interest may be adjusted to avoid "problematic" regions, such as calcifications within the subject.

As used herein, cardiac region refers to a region of the patient that includes the heart. In some cases, the cardiac region may also include other components of the chest of the subject such as the rib cage of the subject.

As used herein, radiotracer uptake may refer to the quantification of the amount of radioactive tracer present within a specific anatomical region or component.

In one aspect, the present disclosure provides a method for diagnosing transthyretin cardiac amyloidosis in a subject. The method can comprise introducing a technetium-99m pyrophosphate radiotracer into a subject; acquiring single-photon emission computed tomography (SPECT) image data of a cardiac region of the subject based on the uptake of the radiotracer; acquiring anatomical image data of the cardiac region of the subject; combining the SPECT image data and the anatomical image data to produce a combined three-dimensional image of the cardiac region; and comparing the radiotracer uptake present within a first volume of interest and a second volume of interest, wherein both volumes of interest are located within the combined image of the cardiac region.

The first volume of interest may be representative of the left ventricle of the subject. The second volume of interest may be representative of the blood pool of the subject. The second volume of interest may be located within the right atrium of the subject.

In another aspect, the present disclosure provides a method for diagnosing transthyretin cardiac amyloidosis in a subject. The method can comprise introducing a radiotracer into a subject; acquiring single-photon emission computed tomography (SPECT) image data of a cardiac region of the subject based on the uptake of the radiotracer; acquiring anatomical image data of the cardiac region of the subject; combining the SPECT image data and the anatomical image data to produce a combined three-dimensional image of the cardiac region; and comparing the radiotracer uptake present within a first volume of interest and a second volume of interest, wherein the first volume of interest is representative of the left ventricle of the subject and the second volume of interest is representative of the blood pool of the subject.

The radiotracer may have a radioisotope. This radioisotope of the radiotracer may be selected from the group consisting of $^{99m}Tc$, $^{123}I$, $^{111}In$, $^{67}Ga$, $^{177}Lu$, $^{201}Ti$, $^{117m}S_n$, $^{125}I$, or any other commonly used gamma ray emitter. The radiotracer may be selected from the group consisting of technetium-99m methylene diphosphonate, technetium-99m 2,3-dicarboxypropane-1,1-diphosphonate, technetium-99m ethane-1-hydroxy-1,1-diphosphonate, and technetium-99m pyrophosphate. The radiotracer may be technetium-99m pyrophosphate. The second volume of interest may be located within the right atrium of the subject.

In the methods described above, the method step of acquiring SPECT image data may occur more than 90, 120, 150, 160, 170, 180, 190, 200, or 210 minutes after the step of introducing the radiotracer. The method step of acquiring SPECT image data may specifically occur about 3 hours after the step of introducing the radiotracer. This incubation period between steps may differ from traditional 1 hour incubation protocol. By using a longer incubation period, there is significantly lower blood pool activity within the subject; this can improve the sensitivity for detecting mild myocardial activity above the nearby blood pool background activity.

In yet another aspect, the present disclosure provides a system for diagnosing transthyretin cardiac amyloidosis in a subject. The system can comprise a source of technetium-99m pyrophosphate radiotracer, means for introducing the technetium-99m pyrophosphate radiotracer into a subject; a single-photon emission computed tomography (SPECT) system configured to acquire SPECT image data of a cardiac region of the subject based on the uptake of the radiotracer; an imaging system configured to acquire anatomical image data of the cardiac region of the subject; a processor configured to combine the SPECT image data and the anatomical image data to produce a combined three-dimensional image of the cardiac region and compare the radiotracer uptake present within a first volume of interest and a second volume of interest, wherein both volumes of interest are located within the combined image of the cardiac region.

Means for introducing the radiotracer may comprise any article or system commonly known in the art for introducing radiotracers into a subject. For example, the radiotracer may be injected into the bloodstream of the subject using a radiotracer injector that has a needle.

The system may further comprise a display configured to present the combined image of the cardiac region to a user. The user may use the information from the combined image on the display to select the location of the first and second volumes of interest within the cardiac region. The first volume of interest may be representative of the left ventricle of the subject. The second volume of interest may be representative of the blood pool of the subject. The second volume of interest may be located within the right atrium of the subject. For example, the volumes of interest (VOI) may be drawn around the entire left ventricle (LV) and a 20 millimeter (mm) diameter spherical VOI within the right atrium (RA) blood pool. In either VOI, bony regions showing asymmetrical distribution of activity may be chosen to be avoided. Further, any areas containing calcifications as seen on CT by the user, such as a calcified lymph node, coronary vessel or valve, may be excluded from the VOI by manual editing of the VOI.

In the methods and systems described herein, the average of the radiotracer uptake present within each volume of interest may be used for comparison. For example, volumes of interests representing mean uptake of the left ventricle (LVmean) might be compared to the mean uptake of the right atrium (RAmean), sternum (STmean) or ribs (RBmean) VOIs. Further, a magnitude of a ratio of the radiotracer uptake in the first volume of interest to that of the second volume of interest may be used to make a diagnosis. For example, comparisons may be used to create LVmean to RAmean ratio (3-D PYP score), LVmean to STmean ratio (3-D LVS) and LVmean to RBmean ratios (3-D LVR). Each of these ratio values may be directly used to make a diagnosis.

A potential advantage of comparing LV to blood pool activity is that it allows for CA assessment in patients with calcified coastal cartilages, bone pathologies such as rib fractures, healing rib lesions, sternotomy (which can be present in patients following a cardiac intervention), and altered thoracic anatomy. Bone uptake can be more variable than blood pool activity. Using a VOI within the right atrium allows for an improved blood pool radiotracer activity reading when compared to other options such as the left ventricle lumen, which is located in a region of higher motion.

In the methods and systems described herein, the anatomical image data may be acquired using a computed tomography (CT) system. For example, the SPECT image data and the anatomical image data may both be acquired using a SPECT-CT hybrid system.

Referring to FIG. 1, a block diagram of an example system 10 is provided that can be configured to carry out techniques, methods, and processes in accordance with the present disclosure. The system may include an imaging system 12 that is coupled to a computer system 14. The imaging system 12 may be a SPECT-CT hybrid system. The coupling of the imaging system 12 to the computer system 14 may be a direct or dedicated network connection, or may be through a broad network 16, such as an intranet or the Internet.

The computer system 14 may be a workstation integrated with or separate from the medical imaging systems 12 or a variety of other medical imaging systems, including, as non-limiting examples, computed tomography (CT) system, magnetic resonance imaging (MRI) systems, positron emission tomography (PET) systems, single photon emission computed tomography (SPECT) systems, and the like. Furthermore, the computer system 14 may be a workstation integrated within the medical imaging system 12 or may be a separate workstation or mobile device or computing system. To this end, the following description of particular hardware and configurations of the hardware of the example computer system 14 is for illustrative purposes. Some computer systems may have varied, combined, or different hardware configurations.

Medical imaging data acquired by the medical imaging system 12 or other imaging system can be provided to the computer system 14, such as over the network 16 or from a storage device. To this end, the computer system 14 may include a communications port or other input port 18 for communication with the network 16 and system coupled thereto. Also, the computer system 14 may include memory and storage capacity 20 to store and access data or images.

In some configurations, the computer system 14 may include one or more processing systems or subsystems. That is, the computer system 14 may include one or more physical or virtual processors. As an example, the computer system 14 may include one or more of a digital signal processor (DSP) 22, a microprocessor unit (MPU) 24, and a graphics processing unit (GPU) 26. If the computer system 14 is integrated into the medical imaging system, a data acquisition unit 28 may be connected directly to the above-described processor(s) 22, 24, 26 over a communications bus 30, instead of communicating acquired data or images via the network 16. As an example, the communication bus 30 can be a group of wires, or a hardwire used for switching data between the peripherals or between any component, such as the communication buses described above.

The computer system 14 may also include or be connected to a display 32. To this end, the computer system 14 may include a display controller 34. The display 32 may be a monitor connected to the computer system 14 or may be integrated with the computer system 14, such as in portable computers or mobile devices.

Figure 2A:
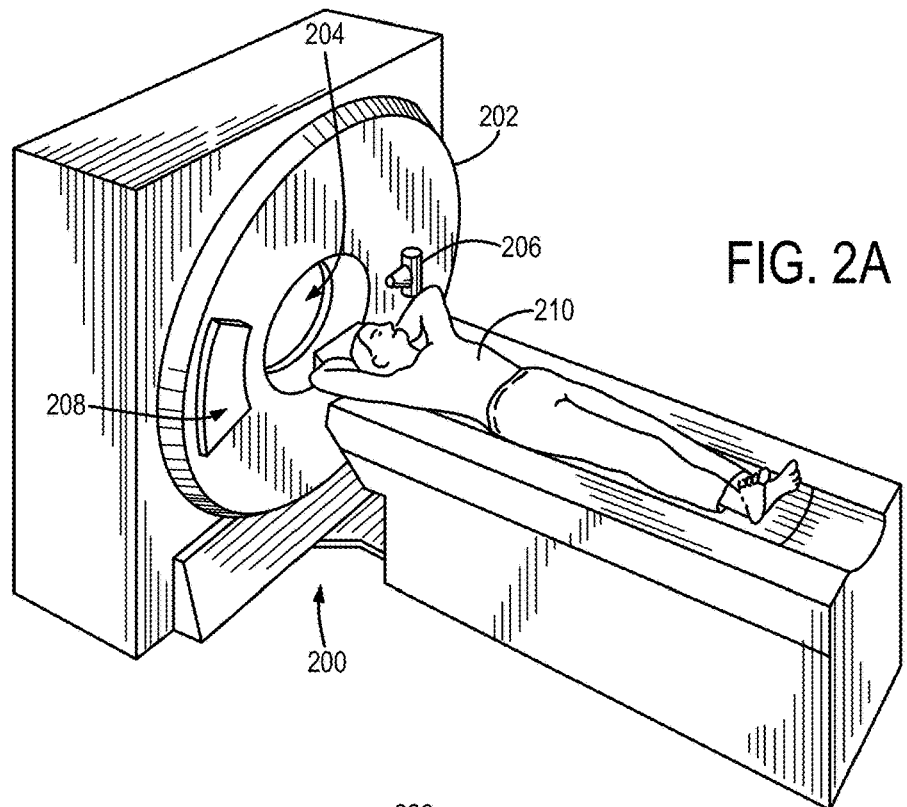
FIG. 2A is a perspective view of an example of an x-ray computed tomography (CT) system that can be used with the systems and methods of the present disclosure.
Figure 2B:
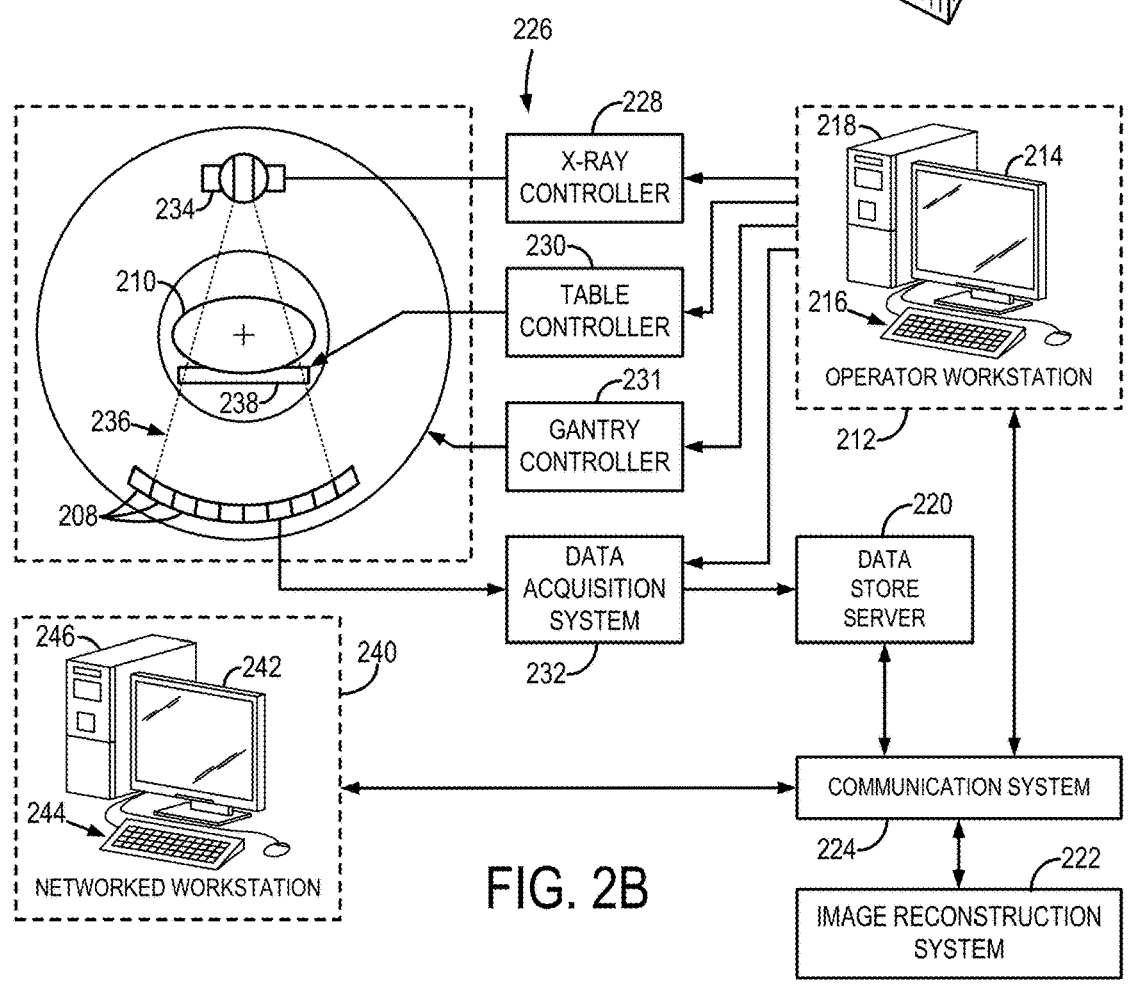
FIG. 2B is a block diagram of a CT system, such as illustrated in FIG. 2A.

Referring to FIGS. 2A and 2B, the imaging system 12 (FIG. 1) may include a CT imaging system 200, which includes a gantry 202 that forms a bore 204 extending therethrough. In particular, the gantry 202 has an x-ray source 206 mounted thereon that projects a fan-beam, or cone-beam, of x-rays toward a detector array 208 mounted on the opposite side of the bore 204 through the gantry 202 to image the subject 210.

The CT system 200 also includes an operator workstation 212, which typically includes a display 214; one or more input devices 216, such as a keyboard and mouse; and a computer processor 218. The computer processor 218 may include a commercially available programmable machine running a commercially available operating system. The operator workstation 212 provides the operator interface that enables scanning control parameters to be entered into the CT system 200. In general, the operator workstation 212 is in communication with a data store server 220 and an image reconstruction system 222 through a communication system or network 224. By way of example, the operator workstation 212, data store server 220, and image reconstruction system 222 may be connected via a communication system 224, which may include any suitable network connection, whether wired, wireless, or a combination of both. As an example, the communication system 224 may include both proprietary or dedicated networks, as well as open networks, such as the Internet.

The operator workstation 212 is also in communication with a control system 226 that controls operation of the CT system 200. The control system 226 generally includes an x-ray controller 228, a table controller 230, a gantry controller 231, and a data acquisition system (DAS) 232. The x-ray controller 228 provides power and timing signals to the x-ray module(s) 234 to effectuate delivery of the x-ray beam 236. The table controller 230 controls a table or platform 238 to position the subject 210 with respect to the CT system 200.

The DAS 232 samples data from the detector 208 and converts the data to digital signals for subsequent processing. For instance, digitized x-ray data is communicated from the DAS 232 to the data store server 220. The image reconstruction system 222 then retrieves the x-ray data from the data store server 220 and reconstructs an image therefrom. The image reconstruction system 222 may include a commercially available computer processor, or may be a highly parallel computer architecture, such as a system that includes multiple-core processors and massively parallel, high-density computing devices. Optionally, image reconstruction can also be performed on the processor 218 in the operator workstation 212. Reconstructed images can then be communicated back to the data store server 220 for storage or to the operator workstation 212 to be displayed to the operator or clinician.

The CT system 200 may also include one or more networked workstations 240. By way of example, a networked workstation 240 may include a display 242; one or more input devices 244, such as a keyboard and mouse; and a processor 246. The networked workstation 240 may be located within the same facility as the operator workstation 212, or in a different facility, such as a different healthcare institution or clinic.

The networked workstation 240, whether within the same facility or in a different facility as the operator workstation 212, may gain remote access to the data store server 220 and/or the image reconstruction system 222 via the communication system 224. Accordingly, multiple networked workstations 240 may have access to the data store server 220 and/or image reconstruction system 222. In this manner, x-ray data, reconstructed images, or other data may be exchanged between the data store server 220, the image reconstruction system 222, and the networked workstations 212, such that the data or images may be remotely processed by a networked workstation 240. This data may be exchanged in any suitable format, such as in accordance with the transmission control protocol (TCP), the Internet protocol (IP), or other known or suitable protocols.

Figure 3:
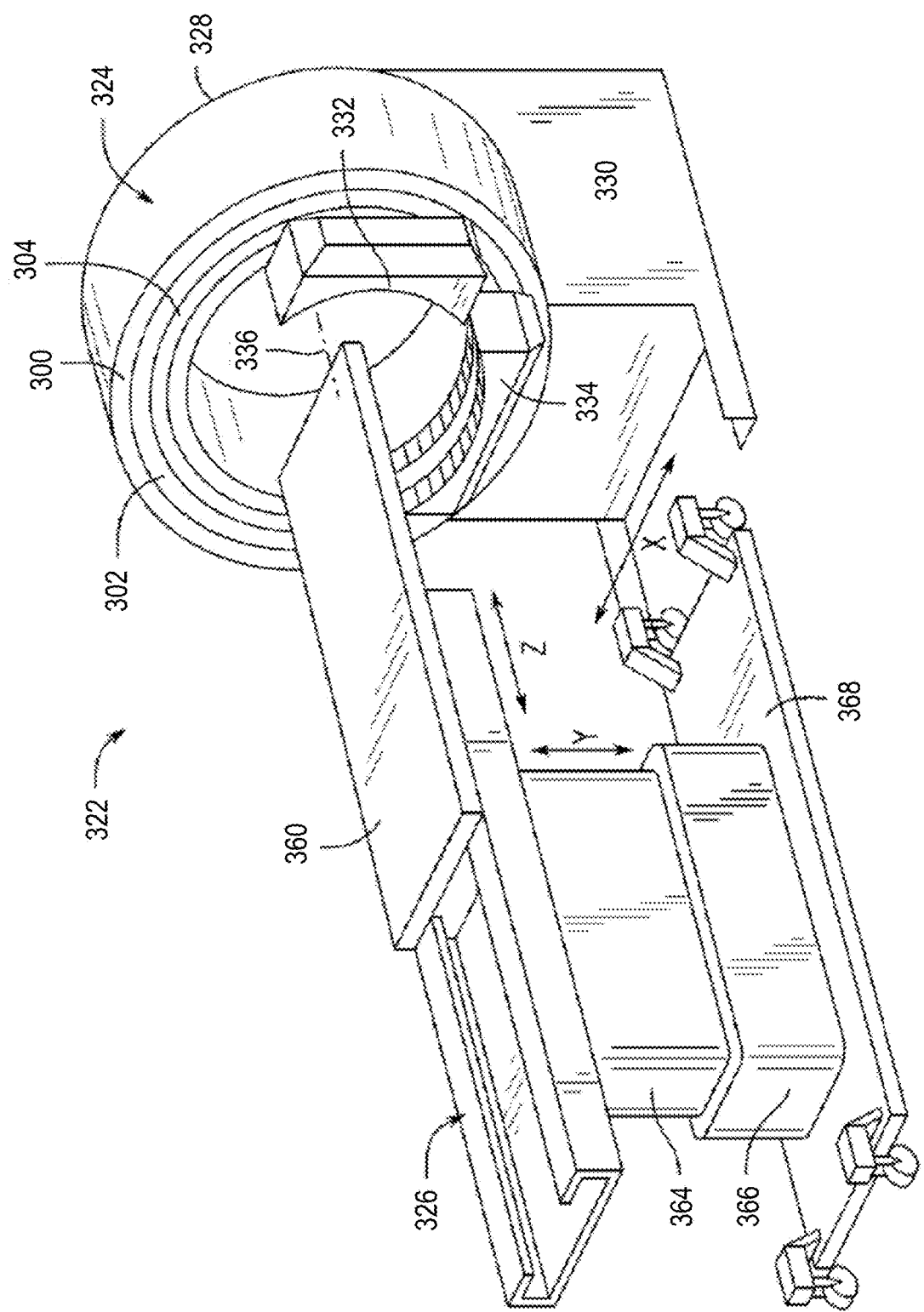
FIG. 3 is a perspective view of an example of a single-photon emission computed tomography (SPECT) system that can be used with the systems and methods of the present disclosure.

Referring particularly to FIG. 3, the imaging system 12 (FIG. 1) may include a SPECT imaging system 322 that is illustrated and includes a tomography machine 324 and a patient support table 326. The table 326 includes a top surface 360 which allows supported movement of the top surface 360 along a scanning or horizontal Z-axis. The top surface 360 is supported by a vertical leg 364 which extends upwardly from a collar 366. The length of the leg 364 can be increased or decreased to raise or lower top surface 360 along a vertical Y-axis. The collar 366 is secured to a dolly 368 having four wheels. Thus, the table 326 enables an operator to position a subject on the top surface 360 in the bore of the tomographic machine 324.

The tomography machine 324 includes a pedestal 330, a gantry 328 and two annular detectors 332, 334. The top surface of the pedestal 330 receives an outer surface of gantry 328 and it houses a motor for rotating moving components of the gantry 328 about a central gantry rotation axis 336 as described in more detail below. The gantry 328 includes an annular race housing 300, which encircles first and second moveable rings 302, 304. Each of the rings 302 and 304 is annular shaped and when the machine 324 is assembled, all of the rings are concentric about imaging axis 336.

The detectors 332 and 334, depending upon configuration, may be stationary, while an annular collimator rotates to acquire different view angles. Alternatively, the detectors 332 and 334 and an associated collimator may be attached to one of the movable rings 302 and 304. Regardless of whether the detectors 332 and 334 are stationary or movable with the rings 302 and 304, the rings 302 and 304 may be unlocked from each other and rotated on their separate rings 302 and 304 to a number of different configurations. For example, they may be oriented 180 degrees apart for one scan and they may be oriented 90 degrees apart for another scan. The rings 302 and 304 are then locked together and rotated in unison during the scan to achieve the prescribed range of view angles.

As will be described, each camera 332, 334 has a collimator associated therewith. A scintillation crystal is positioned to absorb gamma emissions and produce light emissions corresponding to each absorbed gamma emission. The light emissions are directed toward an array of closely packed PMTs. Detected light emissions cause the PMTs to produce analog signals which are sent to a computer system that uses the signals to compute M and N coordinates of each gamma emission absorbed in terms of analog signal magnitudes.

Figure 4:
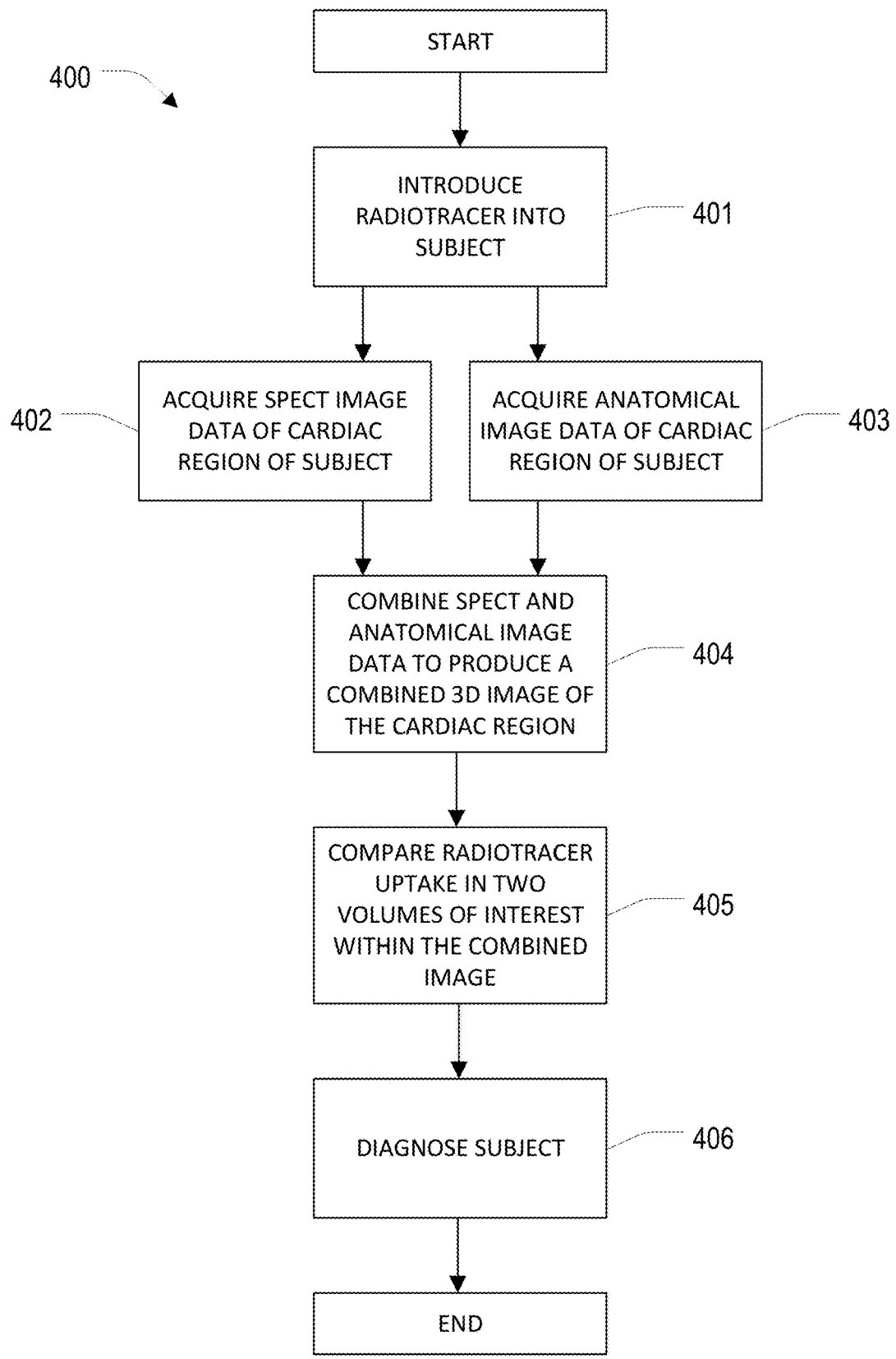
FIG. 4 is a method flow diagram for diagnosing transthyretin cardiac amyloidosis.

Referring to FIG. 4, a method flow diagram 400 incorporating the methods of the present disclosure is presented. The method flow diagram 400 includes a step wherein a radiotracer is introduced into a subject 401. Subsequent steps comprise acquiring SPECT image data 402 and acquiring anatomical image data 403 or a cardiac region of a subject. The method step of combining SPECT and anatomical image data to produce a combined 3D image 404 is provided. A step of comparing the radiotracer uptake in two volumes of interest within the combined image 405 is then presented. Diagnosing the subject 406 is presented as the last method step.

The above systems and methods for diagnosing transthyretin cardiac amyloidosis in a subject may further comprise additional steps and equipment for treating transthyretin cardiac amyloidosis. In this manner, the above systems and methods may diagnose and treat transthyretin cardiac amyloidosis. The additional steps may comprise treating the subject with at least one technique or medicament to alleviate or cure the transthyretin cardiac amyloidosis. For instance, the step may comprise providing at least one technique of medicament that blocks TTR synthesis at the translational level in hepatocytes, stabilizes the TTR tetramer to inhibit the rate-determining step of amyloidogenesis, or disrupts and clears the ATTR amyloid fibril. A medicament may be administered using an injector, such as a syringe.

EXAMPLES

The following Examples are provided in order to demonstrate and further illustrate certain embodiments and aspects of the present disclosure and are not to be construed as limiting the scope of the disclosure.

Example 1

In this experimental study, 33 sequential clinical PYP scans in 33 patients (23 ATTR, 5 AL, 5HFpEF) with endomyocardial biopsy (EMB) confirmed diagnoses were included. Clinical history, echocardiographic findings, and biochemical variables were noted from electronic medical records. Quantitative analysis was performed on SPECT/CT (3-D, volumetric) and planar scintigraphy (2-D) images, taken 3 hours after injection of PYP. On SPECT/CT, volumes of interest (VOIs) were drawn around the entire left ventricle (LV) while carefully avoiding calcifications, within the right atrium (RA) blood pool, around the sternum (ST) and around the right ribs (RB). Mean uptake values were used to calculate the 3-D PYP score (LVmean:RAmean), 3-D LVS (LVmean:STmean) and 3-D LVR (LVmean:RBmean). On planar scintigraphy images, heart to contralateral (HCL) ratio was calculated by dividing the counts in a region of interest (ROI) drawn over the heart by counts in the same sized ROI placed in the contralateral chest. For comparison, five different HCL ratios ($HCL_s$, $HCL_f$, $HCL_o$, $HCL_{nA}$ and $HCL_{nT}$) were calculated using five different ROI methods. Validation procedure included VOIs and ROIs measurements and analysis by 2 independent technologists and 2 independent nuclear medicine physicians, respectively.

Materials and Methods

Figure 5:
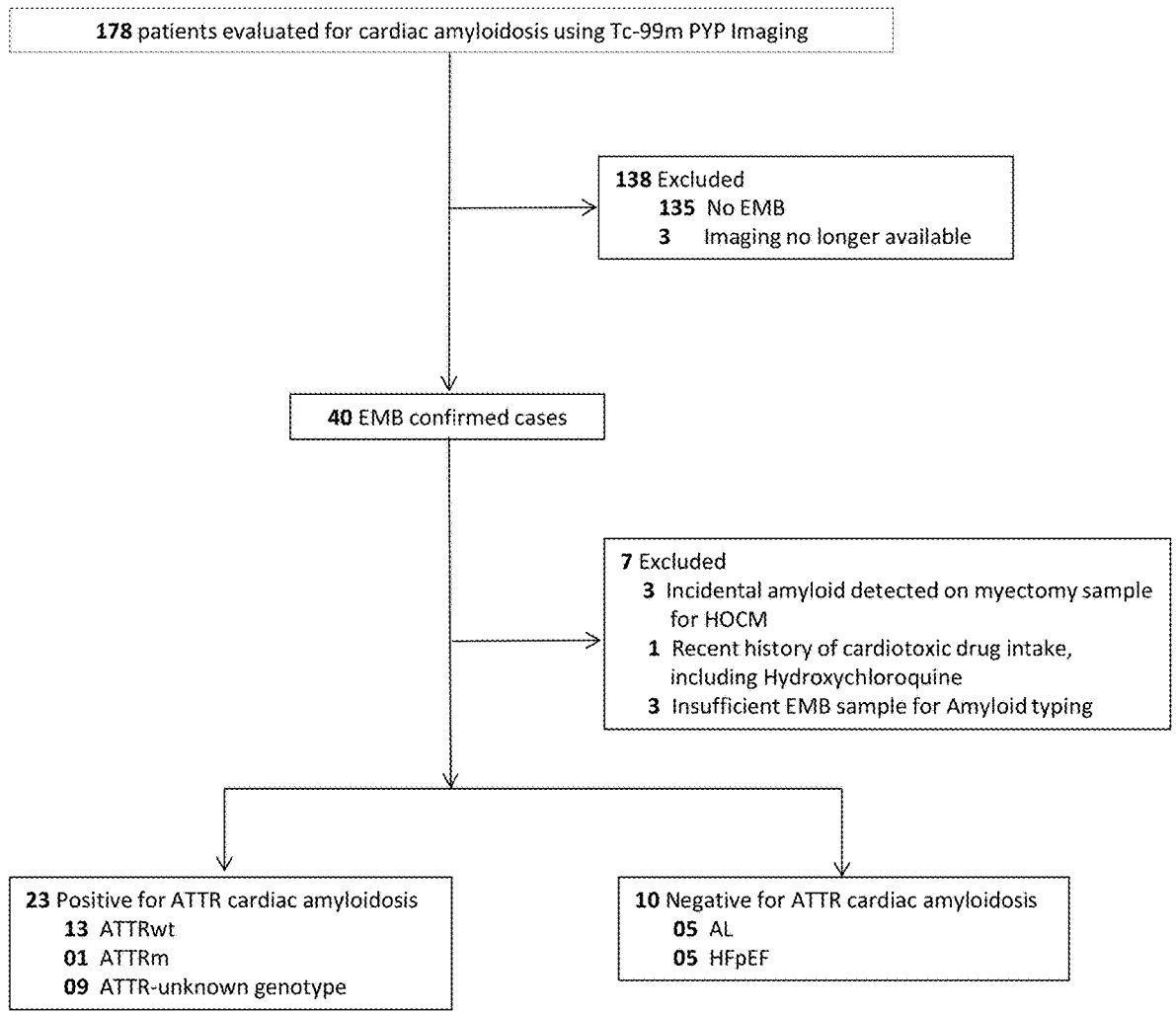
FIG. 5 is a block flow diagram of the experimental patient selection process for Example 1. (Abbreviations: Tc 99m PYP=Technetium 99m pyrophosphate; EMB=Endomyocardial biopsy; ATTR=Transthyretin related amyloid; AL=light chain amyloid; ATTRm=mutated transthyretin; ATTRwt=wild-type transthyretin; HFpEF=heart failure with preserved ejection fraction; HOCM=hypertrophic obstructive cardiomyopathy.)

Study Population: 178 patients underwent 189 sequential $^{99m}$Tc-PYP SPECT/CT and planar scintigraphy cardiac imaging at our institution for indication of cardiac amyloidosis. We excluded patients who had (a) no EMB, (b) history of cardiotoxic drug such as hydroxchloroquine intake for more than 1 month with last dose within the last 6 months [Ref. 35], (c) history of myocardial infarct in last 2 months, (d) insufficient EMB tissue specimen for amyloid typing and (e) incidental deposits of amyloid detected on myectomy tissue specimen, where myectomy was done for unrelated (non-amyloid suspected) condition including in patients with hypertrophic obstructive cardiomyopathy (HOCM) and (f) history of prior nuclear imaging within 48 hours of the PYP scan. After exclusion, we identified 33 patients with EMB confirmed amyloidosis or lack thereof. Of these 33 patients, 23 were positive for ATTR-CM, 5 were positive for AL and 5 were negative for amyloid with HFpEF. Of 23 ATTR patients, 14 patients underwent genotyping and were classified as wild type ATTR (ATTRwt) and mutant ATTR (ATTRm) accordingly. A flowchart detailing the patient selection process is shown in FIG. 5.

Amyloid deposits in EMB tissue specimens were histologically confirmed using sulfated Alcian blue and/or Congo red staining. Formalin-fixed paraffin-embedded (FFPE) tissue biopsies were stained with sulfated Alcian blue and/or Congo red dye and viewed under cross polarized light microscopy. Presence of apple green birefringence on Congo red staining or green stained deposits on sulfated Alcian blue were considered positive for amyloid [Ref. 10,36]. For amyloid typing, areas of Congo-red or Alcian sulfated blue positive deposits from FPE tissue samples were laser micro-dissected from the plastic slide preparations and subjected to liquid chromatography tandem mass spectrometry (LC-MS/MS) [Ref. 16] ATTR subtyping into ATTRm (mutations in TTR gene) and ATTRwt (non-mutated TTR gene) was done by genotyping.

All patients electronic medical records (EMR) were evaluated for patient demographics, body mass index (BMI), age at diagnosis and last follow-up, serum cardiac biomarkers including troponin T and amino terminal pro-B-type natriuretic peptide (NT pro-BNP), serum light chains (K and A), monoclonal band during immunofixation of serum or urine, echocardiography findings including left ventricular (LV) mass, LV ejection fraction (LVEF), left atria (LA) size, interventricular septum thickness in diastole (IVSD), LV posterior wall thickness (LVPW), stroke volume (SV), stroke volume index (SVI), myocardial volume (MV), myocardial contraction fraction (MCF) and longitudinal strain.

Abnormal serum free light chain (FLC) ratio was defined as ratio of K (kappa) FLCs to A (lambda) FLCs<0.26 or >1.65. AL clone was defined as the presence of a monoclonal band during immunofixation of serum or urine. SVI was defined as SV per body surface area. MCF was defined as volumetric index of myocardial shortening and it was calculated as a ratio of SV to MV. Myocardial longitudinal strain (measure of left ventricular dysfunction) of more than −18% (e.g. −13%) was considered abnormal.

Image Acquisition: $^{99m}$Tc SPECT/CT and planar cardiac imaging were performed on a hybrid SPECT/CT system (Philips Precedence) using gamma camera with low energy high resolution collimator. All patients were administered a dose of 10-20±10% mCi $^{99m}$Tc-PYP intravenously. Anterior chest planar images were obtained at 15 minutes and 3 hours after the injection with patients in supine position, using a 256×256 matrix and a rate of 5 min per view. SPECT/CT acquisition of the chest was performed immediately after the 3 hour planar imaging. SPECT images were acquired using 128×128 matrix, 128 views with 30 second per view. Low-dose CT images were obtained for anatomic localization (slice thickness of 3 mm; 3 mm increment; 120 kVp and 60 mAs/slice).

Image Analysis (a) Development of 3-D (SPECT/CT) and 2-D (Planar scintigraphy) based quantitative measures (various HCL ratios).

Figure 6:
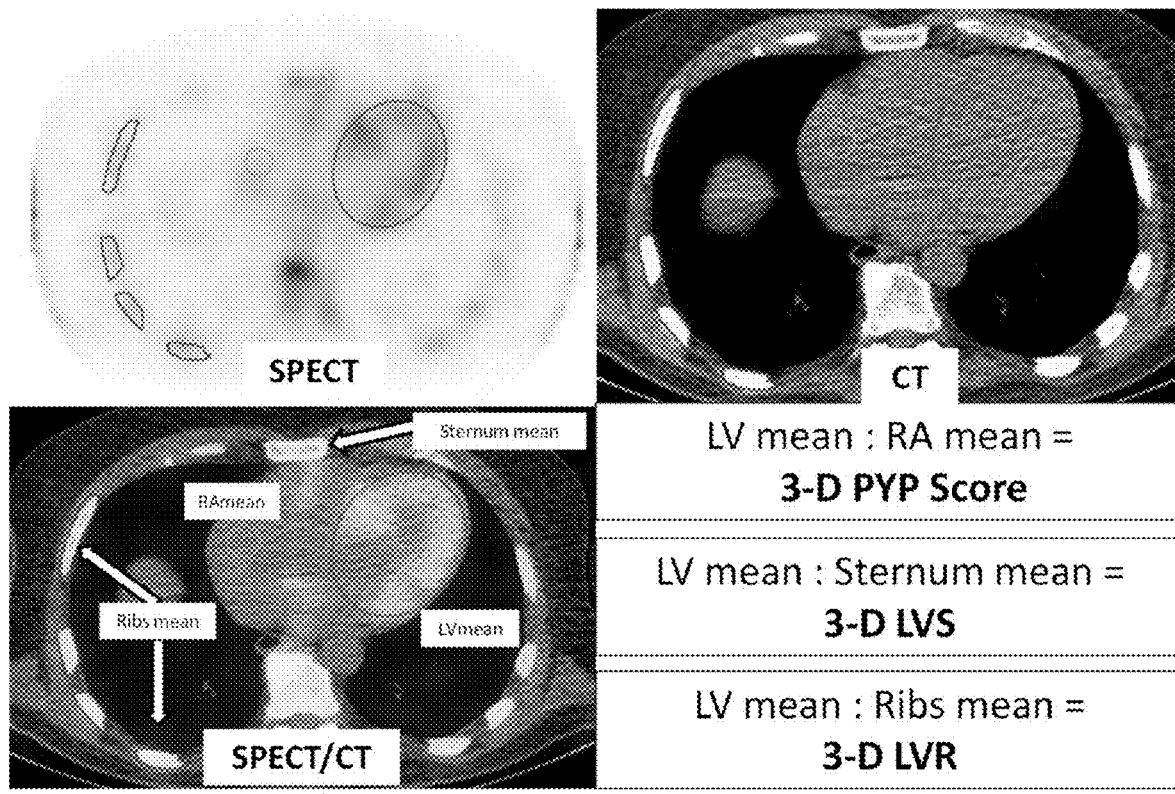
FIG. 6 shows experimental SPECT/CT images and the location of the sternum, ribs, left ventricle, and right atrium areas that were used to calculate the 3D PYP score, 3D LVS score, and the 3D LVR score in the experiment of Example 1.

3-D (SPECT/CT) analysis: 3-D quantitative myocardial uptake of PYP was performed on SPECT/CT images using the MIM software (MIM Software Inc., Cleveland, Ohio). On SPECT/CT fused images, the volumes of interest (VOIs) were drawn around the entire left ventricle (LV), a 20 mm diameter spherical VOI within the right atrium (RA) blood pool, around the sternum and around the right ribs. Bony regions showing asymmetrical distribution of activity were avoided. In the left ventricle, any areas containing calcifications as seen on CT, such as a calcified lymph node, coronary vessel or valve, were excluded from the VOI by free-hand modifications of the VOI. In case of asymmetric uptake in multiple right ribs, the left ribs were used for analysis. Mean uptake of the LV (LVmean), RA (RAmean), sternum (STmean) and ribs (RBmean) VOIs were measured. These were used to create LVmean to RAmean ratio (3-D PYP score), LVmean to STmean ratio (3-D LVS) and LVmean to RBmean ratios (3-D LVR). VOIs were drawn by a blinded research trainee (MBBS) and were reviewed and modified by board certified nuclear medicine physician with 6 years of clinical experience. FIG. 6 shows the various 3-D quantitative measurement techniques.

Figure 7:
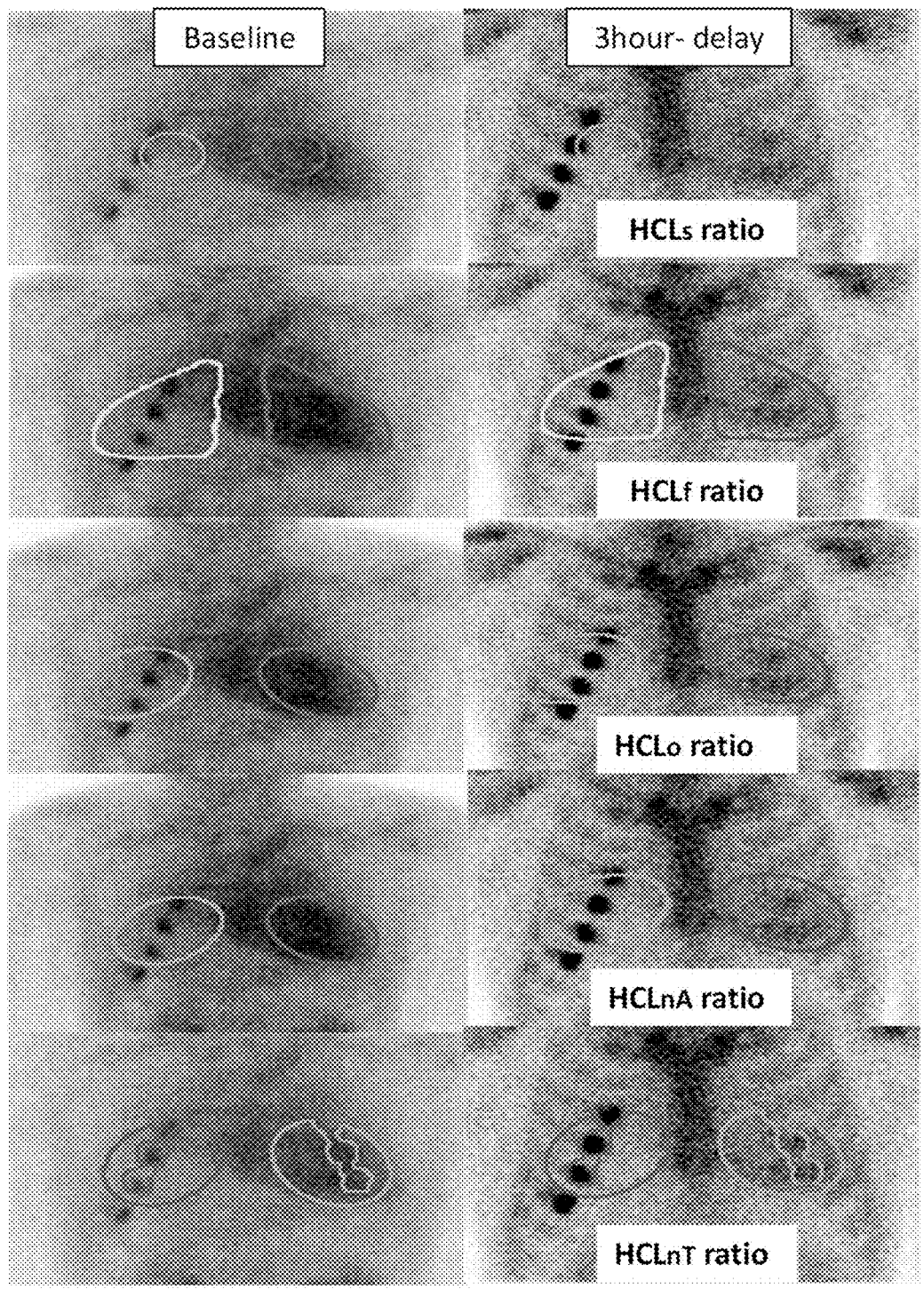
FIG. 7 shows experimental planar scintigraphy images produced with different HCL ratios in the experiment of Example 1.

2-D (Planar scintigraphy) analysis: The 2-D quantitative analysis was performed on planar scintigraphy images using MIM software (MIM Software Inc., Cleveland, Ohio). A region of interest (ROI) was drawn over the heart on anterior planar chest blood pool images taken 15 minutes after the PYP injection, for better visualization of cardiac outline; and a same sized ROI was placed over the contralateral chest. Both the ROIs were copied on anterior planar chest images taken 3 hours after the PYP injection in identical positions, using the MIM software and adjusted to avoid sternum activity. A heart to contralateral (HCL) ratio was calculated by dividing the counts in ROI drawn over the heart by counts in the same sized ROI placed in the contralateral chest on anterior planar chest images taken 3 hours after the PYP injection. HCL ratio is a validated tool for assessment of ATTR-CA [Ref. 31]. Here we calculated HCL ratios using different measurement techniques. In total, five different ROI measurement techniques were used. The ROI drawn in these techniques were as follows: (a) $ROI_1$, for $HCL_s$ (small)—small 50 mm circle contained within the myocardium, (b) $ROI_2$, for $HCL_f$ (free-hand)—free-hand draw following the outline of the myocardium, (c) $ROI_3$, for $HCL_o$ (oval)—encompassed the entire heart in an oval shape including some background, (d) $ROI_4$, for $HCL_{nA}$ (no atria)—same oval ROI but moved lateral to the right atria of the heart on the contralateral side and (e) $ROI_5$, for $HCL_{nT}$ (no trauma)—same oval but excluded osseous structures showing asymmetrical PYP uptake, by free-hand modifications. ROIs were drawn by a nuclear technologist student who was blinded to the clinical and pathological findings and were reviewed and modified by board certified nuclear medicine physician. FIG. 7 shows the various 2-D quantitative measurement techniques.

(b) Multi-reader validation of 3-D (SPECT/CT) and 2-D (Planar scintigraphy) based best quantitative measures:

Training and Image Analysis: 2 board certified nuclear medicine technologists practiced drawing ROIs ($HCL_{nT}$) and VOIs (3-D PYP score) in 10 new training cases under supervision of 2 board certified nuclear medicine physicians. Following training, the nuclear medicine technologists independently performed VOIs and ROIs measurements in 33 study cases. The technologists were blinded to the clinical and pathological findings.

Multireader Review: All the SPECT/CT and planar scintigraphy images were independently reviewed using MIM software (MIM Software Inc., Cleveland, Ohio) by 2 board certified nuclear medicine physicians. They were blinded to clinical and pathological findings. Diagnosis of ATTR-CA was based on a combined quantitative (score) and qualitative (visual) based analysis and it was graded on a 5 point diagnostic confidence scale (1=not at all confident, 2=not very confident, 3=neutral, 4=confident, 5=very confident).

Figure 8:
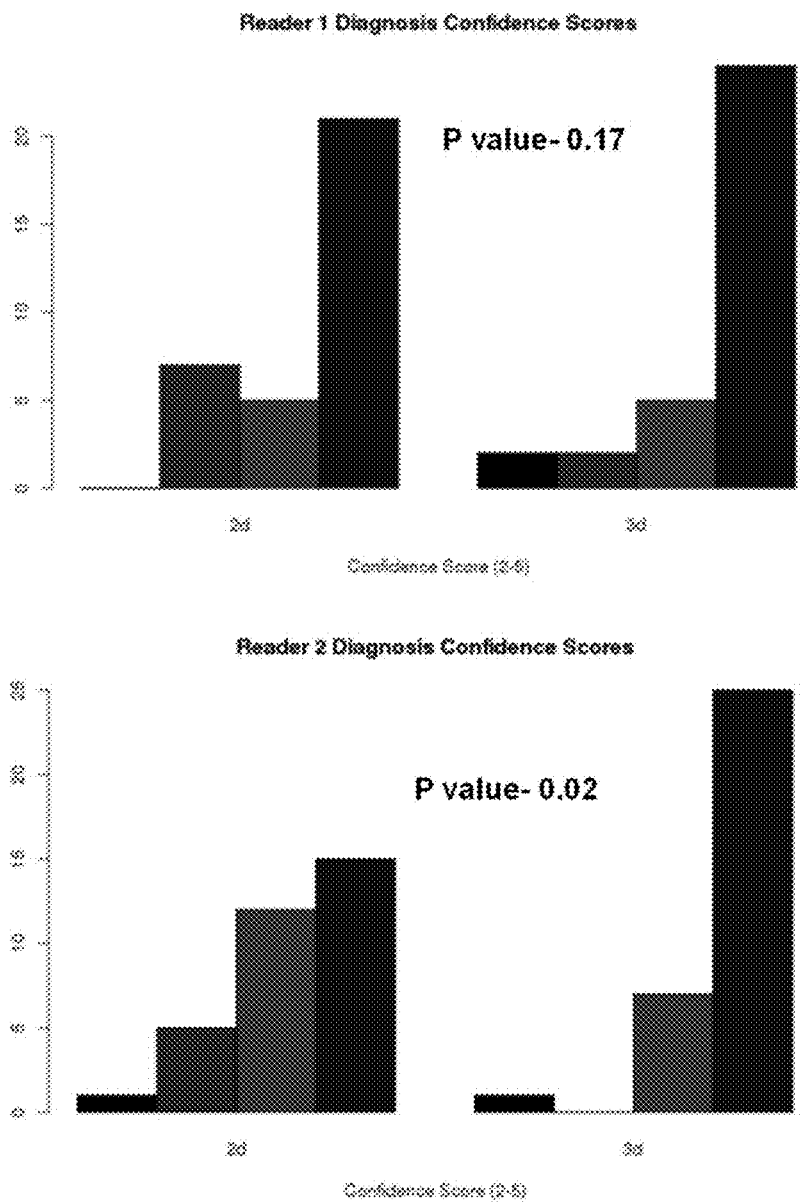
FIG. 8 shows experimental plots of distribution of confidence scores for two readers in the study of Example 1. Increase in reader confidence (statistically significant for reader 1 and a positive trend observed for reader 2) on SPECT/CT compared to the planar scintigraphy for diagnosis of ATTR-CA.

Statistical Analysis: Continuous variables were expressed as a mean or median with range and categorical data as percentage. Chi-square test was used to compare the categorical variables sensitivity and specificity to detect ATTR-CA were calculated for each reader and modality combination using standard 2×2 tables. Receiver operating characteristic (ROC) curves were generated to determine the area under the curve (AUC) and the sensitivity and specificity at different cutoffs for different HCL ratios and 3-D SPECT/CT methods. For the multi-reader study, ROC curves were generated for each technologist and AUC's were compared between 2-D HCL score and 3-D PYP score using DeLong's test. Inter-rater agreement between 2-D and 3-D technologist scores was assessed by intra-class correlation coefficient (ICC) and for reader diagnosis by kappa score. Reader confidence scores were compared between 2-D and 3-D images by chi-squared test. P-values of less than 0.05 were considered statistically significant. All statistical analyses for the multi-reader portion were conducted in R version 3.4.2 except for Kappa confidence intervals which were completed in SAS version 9.4 (SAS Institute Inc., Cary, N.C.). The diagnosis confidence scores of each reader are presented in FIG. 8.

Results

Patient Characteristics: 33 patients (31 males and 2 females) formed the final study population, including 23 ATTR-CA (69.7%), 5 AL-CA (15.2%), 5 HFpEF (15.2%) patients. The mean age of presentation was 73.2 years (range 58-87 years). Patients predominantly had NYHA class II or III symptoms (n=11, 91.7%). Of 23 ATTR-CA patients, genotyping was done in 14 (60.9%) patients, of which 13 (92.9%) had ATTRwt and 1 (7.1%) had ATTRm (V142I). ATTR-CA patients had higher serum albumin, lower LVEF and higher longitudinal strain than non-ATTR-CA patients (p <0.05). Monoclonal protein were detected in 4 (80%) cases with AL-CA, and in 2 (12.5%) patients with ATTR-CA. Abnormal SFLC ratio was detected in 4 (80%) cases with AL-CA, and in 6 (33.3%) patients with ATTR-CA and 1 (33.3%) patients with non-amyloid HFpEF. The patient characteristics are summarized in Table 1.

TABLE 1

Patient characteristics

| Characteristics | ATTR Cardiomyopathy (n = 23) | Non-ATTR Cardiomyopathy[a] (n = 10) | P Value |
|---|---|---|---|
| Demographic | | | |
| Age, mean (range), y | 73.3 (58-84) | 73 (61-87) | 0.90 |
| Male sex, number (%) | 22 (95.7) | 9 (90) | 0.53 |
| BMI | 26.4 (21.1-35.3) | 27 (22.5-36.0) | 0.70 |
| Biochemical profile | | | |
| Serum Albumin, mean (range), g/dL | 3.8 (3.3-4.5) | 3.3 (2.7-3.9) | 0.003 |
| Serum Creatinine, mean (range), mg/dL | 1.3 (0.8-2.3) | 1.4 (0.9-2.8) | 0.39 |
| Serum Calcium, mean (range), g/dL | 9.4 (8.5-11) | 9.2 (8.3-10) | 0.41 |
| Troponin T, mean (range), ng/mL | 0.03 (0.00-0.2) | 0.02 (0.00-0.1) | 0.35 |
| NT pro-BNP, mean (range), pg/mL | 2785.6 (302-10322) | 2372.3 (422-4917) | 0.66 |
| Abnormal SFLC ratio, number (%) | 6 (33.3) | 5 (55.6) | 0.27 |
| Presence of Clone, number (%) | 2 (12.5) | 4 (50) | 0.045 |
| Echocardiography | | | |
| LVEF, mean (range), % | 49.2 (22-65) | 61.4 (46-72) | 0.013 |
| LA size, mean (range), mm | 49.3 (31-71) | 45.1 (30-83) | 0.47 |
| IVSD, mean (range), mm | 15.1 (10-20) | 16.6 (13-22) | 0.18 |
| LVPW, mean (range), mm | 14.9 (10-22) | 14.3 (12-17) | 0.63 |
| RWT, mean (range), mm | 4.4 (1-9) | 6.2 (5-8) | 0.06 |
| Lvmass, mean (range), g | 298.5 (175-456) | 296.3 (208-389) | 0.93 |
| SV, mean (range), mL | 65.1 (28-136) | 78.6 (51-140) | 0.40 |
| SVI, mean (range), mL/m$^2$ | 32.6 (16-59) | 39.4 (28-64) | 0.19 |
| Myocardial Volume, mean (range), mL | 241.7 (118.3-438) | 219.7 (102.9-374) | 0.57 |
| MCF, mean (range), g/m$^2$ | 30.6 (12-57.8) | 39.7 (19.2-55.3) | 0.15 |
| Longitudnal strain, mean (range), % | −9.7 (−14 to −4) | −12.8 (−18 to −8) | 0.017 |

Abbreviations: BMI = Body mass index; NYHA = New York Health association; NT pro-BNP = Amino terminal pro-B type natriuretic peptide; SFLC ratio = Serum free light chain ratio; LVEF = Left ventricular ejection fraction; LA = Left atrium; IVSD = Inter-ventricular septal thickness at diastole; LVPW = Left posterior wall thickness at diastole; RWT = Relative wall thickness; LV mass = Left ventricular mass; SV = Stroke volume; SVI = Stroke volume index; MCF = Myocardial contraction fraction.
[a]5 patients with AL cadiac amyloidosis and 5 patients with heart failure with preserved ejection fraction.

Development of 3-D (SPECT/CT) and 2-D (Planar scintigraphy) Based Quantitative Measures: Mean value of SPECT/CT based 3D-PYP score, 3-D LVS and 3-D LVR and planar scintigraphy based HCL ratios were significantly higher in ATTR-CA patients compared with non-ATTR patients (P<0.001). 3-D PYP score showed the best diagnostic accuracy (Cut-off=1.1, sensitivity and specificity=100% with AUC of 1.00) for detecting ATTR-CA among all SPECT/CT and planar scintigraphy based measures. Among planar scintigraphy based measures, HCL$_{nT}$ showed best diagnostic performance (Cut-off=1.3, sensitivity=95.7%, specificity=90%, with AUC of 0.97) for detecting ATTR-CA. The rest of the methods were all slightly inferior. The diagnostic performance of SPECT/CT and planar scintigraphy based methods is summarized in

TABLE 2

Table 2. Tc-99m PYP SPECT/CT and Planar Scintigraphy Diagnostic Accuracy

| Method | ATTR Cardiac Amyloidosis[a] (Mean ± S.D.) | Non-ATTR Cardiac Amyloidosis[b] (Mean ± S.D.) | P Value | Sensitivity (%) For ATTR Cardiac Amyloidosis (cut-off value) | Specificity (%) For ATTR Cardiac amyloidosis (cut-off value) | Area under the curve (AUC) |
|---|---|---|---|---|---|---|
| | | EMB confirmed patients (33 patients) | | | | |
| SPECT/CT | | | | | | |
| 3-D PYP score | 1.7 ± 0.5 | 0.8 ± 0.2 | <0.001 | 100 (1.1) | 100 (1.1) | 1.000 |
| 3-D LVS | 1.1 ± 0.4 | 0.5 ± 0.2 | <0.001 | 94.1 (0.6) | 80 (0.6) | 0.924 |
| 3-D LVR | 1.6 ± 0.6 | 0.8 ± 0.3 | <0.001 | 87.0 (1.1) | 80 (1.1) | 0.907 |
| Planar scintigraphy | | | | | | |
| $HCL_s$ | 1.6 ± 0.3 | 1.1 ± 0.2 | <0.001 | 100 (1.3) | 80 (1.3) | 0.965 |
| $HCL_f$ | 1.5 ± 0.3 | 1.1 ± 0.1 | <0.001 | 95.7 (1.3) | 80 (1.3) | 0.950 |
| $HCL_o$ | 1.5 ± 0.3 | 1.1 ± 0.1 | <0.001 | 95.7 (1.3) | 80 (1.3) | 0.922 |
| $HCL_{nA}$ | 1.6 ± 0.3 | 1.2 ± 0.2 | <0.001 | 100 (1.3) | 80 (1.3) | 0.922 |
| $HCL_{nT}$ | 1.5 ± 0.3 | 1.1 ± 0.1 | <0.001 | 95.7 (1.3) | 90 (1.3) | 0.974 |

Abbreviations: Tc 99m PYP = Technetium 99m pyrophosphate; SPECT/CT = Single photon emission computed tomography and computed tomography; EMB = Endomyocardial biopsy; 3-D = Three dimensional (volumetric); PYP score = Left ventricle mean uptake to right atrium mean uptake ratio; LVS = Left ventricle mean uptake to sternum mean uptake ratio; LVR = left ventricle mean uptake to ribs mean uptake ratio; HCL = Heart to contralateral ratio; $HCL_s$ = HCL ratio calcuted using small region of interests; $HCL_f$ = HCL ratio calcuted using free-hand region of interests; $HCL_o$ = HCL ratio calcuted using oval region of interests; $HCL_{nA}$ = HCL ratio calcuted using oval region of interests excluding right atria; $HCL_{nT}$ = HCL ratio calcuted excluding adjacent osseous structres by drawing free hand region of interests.
[a]23 EMB confirmed; 20 non-cardiac tissue biopsy and echocardiographic findings confirmed.
[b]10 EMB confirmed (5 patients with AL cadiac amyloidosis and 5 patients with heart failure with preserved ejection fraction)

Multi-reader review of 3-D (SPECT/CT) and 2-D (Planar scintigraphy) Based Quantitative Measures: (I) Based on only quantitative assessment: For detection of ATTR-CA, the SPECT/CT based 3D-PYP score using cut-off 1.1, showed sensitivity of 95.7 and 100% (for two technologists), and specificity of 80 and 90%, with AUC 0.90 and 0.97. In comparison, the $HCL_{nT}$ (cut-off=1.3), showed similar sensitivity 95.7% (both technologists) but lower specificity of 70% (both technologists) with AUC of 0.93 and 0.91.

(II) Based on combined quantitative and qualitative assessment (reader based assessment): For detection of ATTR-CA, the SPECT/CT based assessment, showed 91.3 and 95.7% sensitivity, and 100% specificity (both readers). In comparison, the Planar Scintigraphy based assessment, showed similar sensitivity 95.7% (both readers) but lower specificity (70 and 90%). In addition, SPECT/CT lead to an increase in reader confidence (statistically significant for reader 1, p value=0.02; and for reader 2, p value=0.17) in comparison to the planar scintigraphy based assessment for diagnosis of ATTR-CA.

(III) Inter-rater agreement: The inter-rater agreement was very good to excellent between the technologists (0.88 to 0.96); and between the physician readers (0.85 to 0.93) for both SPECT/CT and planar scintigraphy based diagnosis of ATTR-CA.

Discussion

In this study, we found that both SPECT/CT and planar scintigraphy based quantitative methods showed a high diagnostic accuracy for differentiation of ATTR-CA from non-ATTR-cardiomyopathy. However, SPECT/CT based 3-D PYP score (LV to RA blood pool activity) showed significantly better performance with higher specificity and increased reader confidence.

There are recognized limitations of 2-D planar scintigraphy imaging and HCL ratios (quantitative measure for PYP uptake) including (a) inability to visualize myocardium independently from overlying structures, and (b) not allowing the visual interpretation of myocardial PYP distribution. These limitations can potentially lead to inaccurate assessment in patients with non-myocardial PYP uptake in the overlying structures such as a recent myocardial infarction, recent thoracic surgery, rib fractures, altered thoracic anatomy, unilateral mastectomy, skeletal muscle damage, valvular, vascular, or nodal calcifications, calcified costal cartilages, myocardial trauma and persistent blood pool activity in patients with renal failure. $HCL_{nT}$, where ROIs were drawn by avoiding areas with asymmetrical bone uptake such as rib fractures or skeletal trauma can address some of these limitations. In our study, this methodology showed best diagnostic accuracy on 2-D scintigraphy.

Figure 9:
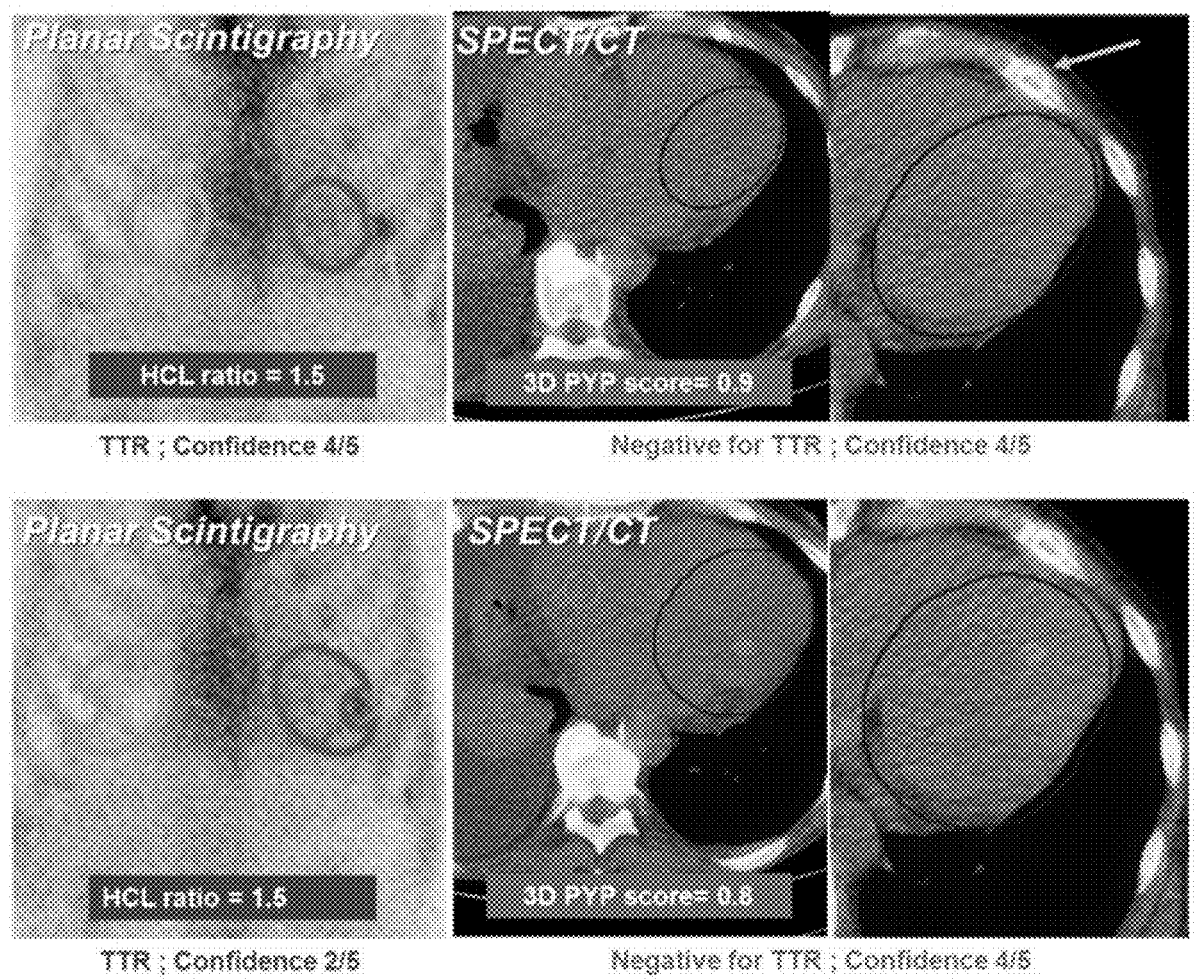
FIG. 9 shows experimental images of a subject with EMB confirmed AL-CA. On planar scintigraphy $HCL_{nT}$ and reader interpretation was positive for TTR-CA. In comparison, on SPECT-CT no PYP uptake in left ventricle wall was seen and 3-D PYP score was reported to be negative for ATTR-CA with high confidence. A focal bone pathology in left rib (arrow) can be noted.

A potential advantage of comparing LV to blood pool activity is that it allows for CA assessment in patients with calcified coastal cartilages, bone pathologies such as rib fractures, healing rib lesions, sternotomy (which can be present in patients following a cardiac intervention) and altered thoracic anatomy [Ref. 41]. Additionally, bone uptake can be variable [Ref. 42]. In our study, a hybrid SPECT/CT scanner was used. The CT component of the hybrid SPECT/CT provides a key advantage by providing better anatomical delineation. This helps in avoiding areas with coronary or lymph node calcifications and overlying soft tissue and bony pathologies while drawing the VOIs (FIG. 9).

Figure 10:
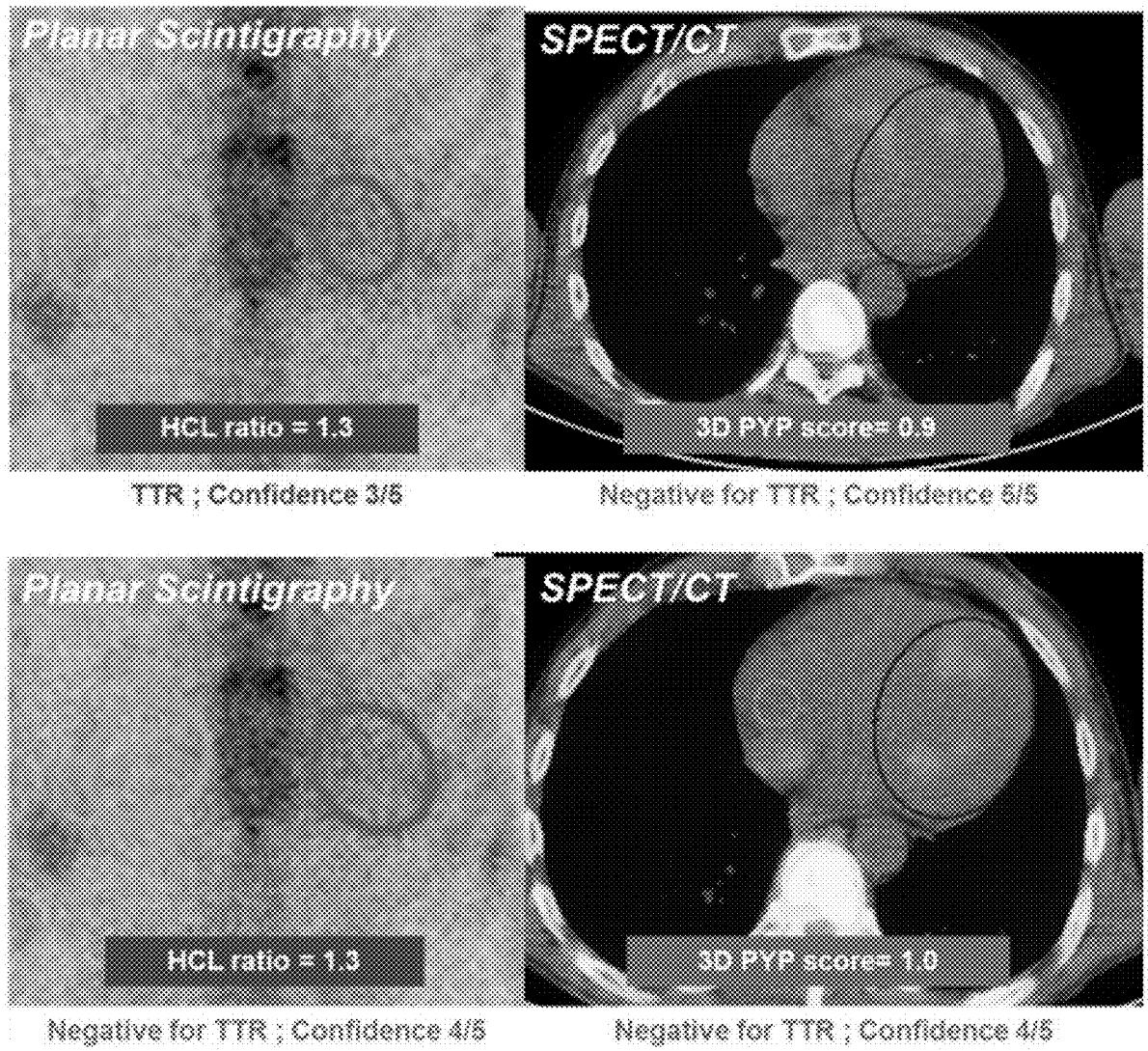
FIG. 10 shows experimental images of a subject with EMB confirmed AL-CA. On planar scintigraphy $HCL_{nT}$ was marginally positive for TTR-CA. However, due to borderline positivity, 1 reader interpreted it as positive and the other as negative. In comparison, on SPECT-CT no PYP uptake in left ventricle wall was seen and 3-D PYP score was reported to be negative for ATTR-CA with high confidence.
Figure 11:
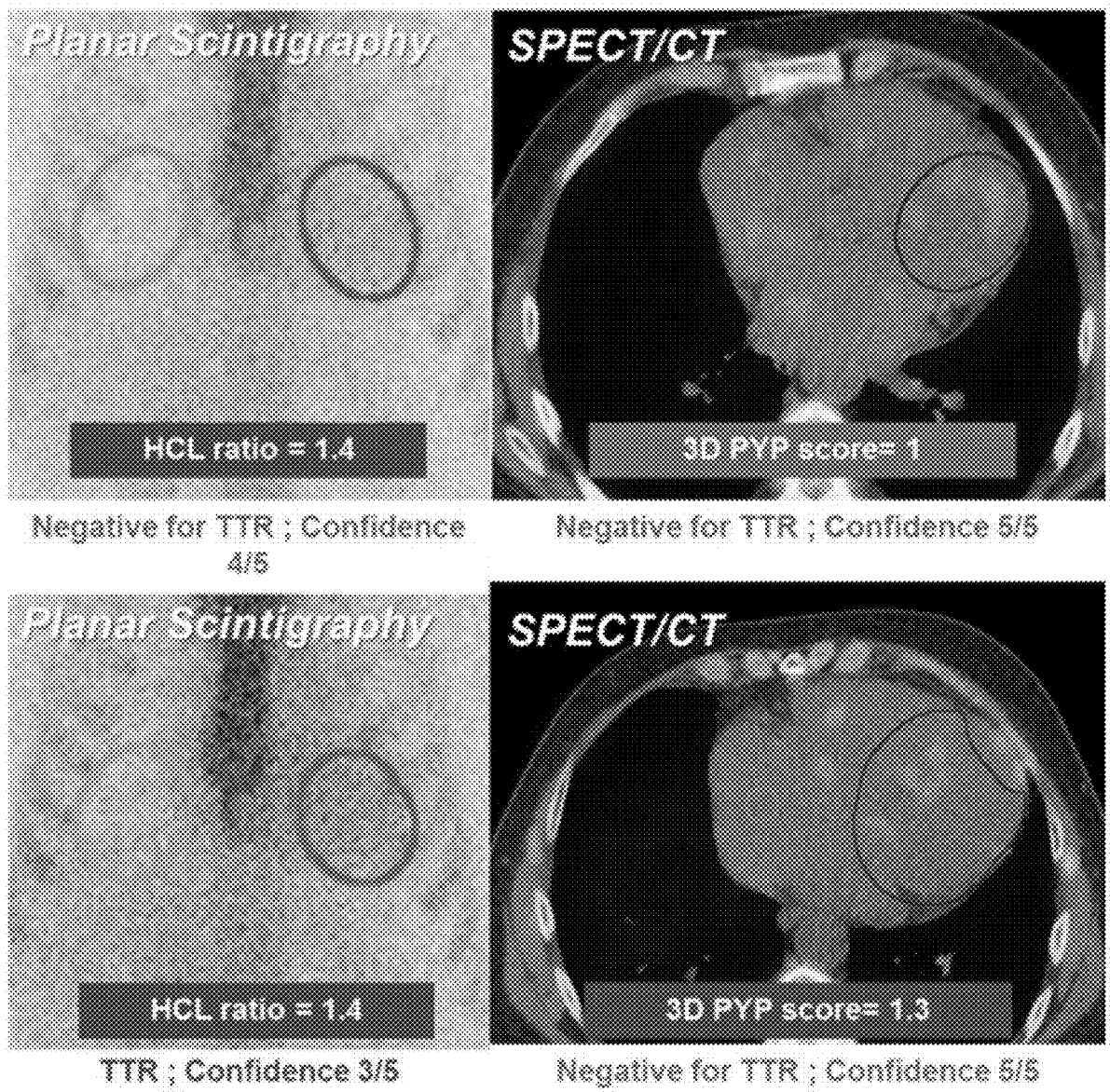
FIG. 11 shows experimental images of a subject with EMB confirmed AL-CA. On planar scintigraphy $HCL_{nT}$ was positive for TTR-CA. However, due to borderline positivity, 1 reader interpreted it as positive and the other as negative. In comparison, on SPECT-CT no PYP uptake in left ventricle wall was seen. The 3-D PYP score was positive for ATTR-CA in one case. However both readers reported it to be negative for ATTR-CA with high confidence.

SPECT/CT also allows for better visual evaluation of cardiac radiotracer uptake and distribution, which can be helpful for differentiating ATTR-CA related PYP uptake from persistent blood pool activity, myocardial trauma, acute myocardial infarcts (MI) which can result in false interpretation on planar scintigraphy (FIG. 10-11). Acute MIs generally show PYP uptake in area with coronary artery distribution and are not diffuse as seen in CA [Ref. 43]. Additionally, ATTR-CA can show various patterns of myocardial PYP uptake. For example, in a study by Gucht et al, an apical sparing pattern (a decreasing gradient from base to apex) of left ventricular myocardial $^{99m}$Tc-HMDP uptake in patients with ATTR-CA, similar to the apical sparing pattern seen on echocardiographic and cardiac MRI was observed

[Ref. 44]. We found that these patterns of PYP uptake can be better appreciated on SPECT/CT based visual evaluation. We observed supportive results in our study as we found that reader based assessment led to an increase in specificity of SPECT/CT in comparison to only quantitative (score based) assessment.

In our study, 12.5% of ATTR-CA patients were positive for monoclonal gammopathy. Monoclonal gammopathy is highly predictive of AL-CA but is not specific as it can also be present in patients with ATTR-CA with reported prevalence ranging from 19 to 31% [Ref. 46-48]. In comparison to the recent study by Castano et al, no significant difference was observed in age, IVSD and troponin T levels in this study between the two groups [Ref. 32].

Patients with HOCM who had TTR diagnosed incidentally on myectomy tissue and those on HCQ therapy were excluded from the study. We have noted that PYP imaging is often negative in patients with incidentally detected amyloid deposition that is perhaps insufficient to cause heart failure, suggesting a minimal threshold of cardiac ATTR may be needed for PYP SPECT/CT to be positive. In a recent case series on HCQ induced cardiotoxicity, increased PYP myocardial activity was noted [Ref. 35]. Therefore, cases with history of prolonged HCQ intake were excluded from our study cohort. There has been little available information on bone radiotracer activity in other amyloidotic cardiomyopathies with some reporting contrasting results. In one EMB confirmed case of apolipoprotein A-I (ApoAI) by Quarta et al. using $^{99m}$TC-DPD, a strong cardiac uptake was noted, which was more than bone uptake [Ref. 59]. However another study reported minimal cardiac uptake of $^{99m}$Tc-DPD in patients with cardiac Apo-AI [Ref. 37]. In few reported cases of cardiac amyloid deposition due to secondary amyloidosis (AA), minimal cardiac PYP retention has been observed [Ref. 41,60].

$^{99m}$Tc-PYP is a bone radiotracer, which is primarily used in evaluation of heart, skeletal muscle, bone malignant conditions like acute myocardial infraction, soft tissue injuries, polymyositis and rhabdomyolysis [Ref. 49,50]. Although several theories have been proposed to explain this preferential binding of bone radiotracers like $^{99m}$Tc-PYP to ATTR-amyloid over AL-amyloid, the precise underlying mechanism is unclear [Ref. 31,51,52]. A recent study suggested the greater density of micro-calcifications associated with ATTR-CA to be the reason for this preferential binding [Ref. 53]. Other bone radiotracers such as Tc-HMDP, Tc-DPD have shown similar diagnostic accuracy to Tc-PYP on planar scintigraphy for ATTR-CA [Ref. 54].

At present, there is a high variability in the utilization, performance, and interpretation of Tc99m-PYP imaging for the diagnosis of cardiac amyloidosis among various centers [Ref. 61]. Different institutions follow different incubation times for PYP scans. At our institution, a 3 hour incubation protocol is used in Tc-99m-PYP imaging studies, as opposed to the common 1 hour incubation protocol. It should be noted that one advantage of imaging at 1 hour is lower bone activity, which is not an issue on SPECT/CT imaging. Theoretically at 3 hours, the sensitivity for detecting mild myocardial activity above the nearby blood pool background activity should be higher because of significantly lower blood pool activity. In a recently published multicenter trial by Castano et al. [Ref. 32], the data showed a better sensitivity (92% vs 88%) and specificity (97% vs 86%) of 1 hour versus 3 hour incubation method based on planar imaging and HCL ratios, respectively. However in the current study with a 3 hour incubation time, the SPECT/CT based 3-D PYP score performed better than both 1 hour and 3 hour incubation planar scintigraphy based methods (sensitivity=91.3-95.7% and specificity=100%).

Finally besides PYP imaging, we envision that other non-invasive procedures like electrocardiogram (ECG), echocardiogram and MRI can be helpful for diagnosis of cardiac amyloidosis. ECG findings including low QRS voltage, conduction defects, non-specific ST changes, pseudo-infraction patterns and left bundle branch block (LBBB) or right bundle branch block (RBBB), [Ref. 8,62, 63] echocardiographic findings such as concentric ventricular thickening with right ventricular involvement, diastolic dysfunction, abnormal longitudinal strain and speckled or granular myocardial appearance ("sparkling") [Ref. 8,22-25] and MRI finding of global, subendocardial late gadolinium enhancement can provide supportive evidence for diagnosing cardiac amyloidosis [Ref. 20,21]. Newer agents like $^{18}$F-florbetapir (both AL and ATTR), $^{11}$C-Pittsburgh B PET/CT(for AL-CA), $^{18}$F-Sodium Fluoride PET/MR (both AL and ATTR) have shown promising results for non-invasive diagnosis of CA [Ref. 55,56-58]. However their potential use and value need further evaluation.

Conclusions: Mean age of presentation was 73.2 years (range 58-87). Patients were predominantly male (n=31, 93.9%) and had NYHA class II or III symptoms (n=11, 91.7%). ATTR-CA patients had significantly higher serum albumin, higher longitudinal strain and lower left ventricular ejection fraction. 3-D PYP score showed the best diagnostic accuracy (Cut-off=1.1, sensitivity and specificity=100%) for detecting ATTR-CA among all SPECT/CT and planar scintigraphy based measures. Among planar scintigraphy based measures $HCL_{nT}$ showed best diagnostic accuracy (Cut-off=1.3, sensitivity=95.7%, specificity=90%) for detecting ATTR-CA. In multi-reader study, SPECT/CT and 3D PYP score showed higher specificity (100% vs 80-90% for SPECT/CT and planar scintigraphy based reader assessment, respectively) and led to an increase in reader confidence. The inter-rater agreement was very good to excellent between the technologists; and between the physician readers for both SPECT/CT and planar scintigraphy based diagnosis of ATTR-CA.

Thus, the SPECT/CT based 3-D PYP score is a reliable method with an excellent sensitivity and specificity for diagnosis of ATTR-CA. 3-D PYP score demonstrated a better diagnostic specificity than 2-D planar scintigraphy HCL ratios and led to increase in reader's confidence for diagnosis of ATTR-CA. Imaging at 3 hours after injection may result in higher sensitivity for ATTR-CA by allowing blood pool activity to resolve.

Thus, the present invention provides systems and methods for enhanced diagnosis and treatment of transthyretin-related cardiac amyloidosis in a subject.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

REFERENCES

1. Bennani Smires Y, Victor G, Ribes D, et al. Pilot study for left ventricular imaging phenotype of patients over 65 years old with heart failure and preserved ejection fraction: the high prevalence of amyloid cardiomyopathy. *Int J Cardiovasc Imaging.* 2016; 32(9):1403-1413.

2. Gonzalez-Lopez E, Gallego-Delgado M, Guzzo-Merello G, et al. Wild-type transthyretin amyloidosis as a cause of heart failure with preserved ejection fraction. *Eur Heart J.* 2015; 36(38):2585-2594.
3. Mohammed S F, Mirzoyev S A, Edwards W D, et al. Left ventricular amyloid deposition in patients with heart failure and preserved ejection fraction. *JACC Heart Fail.* 2014; 2(2):113-122.
4. Grogan M, Scott C G, Kyle R A, et al. Natural History of Wild-Type Transthyretin Cardiac Amyloidosis and Risk Stratification Using a Novel Staging System. *J Am Coll Cardiol.* 2016; 68(10):1014-1020.
5. Scully P, Treibel T A, Fontana M, et al. Prevalence of Cardiac Amyloidosis in Patients Referred for Transcatheter Aortic Valve Replacement. *J Am Coll Cardiol.* 2018; 71(4):463-464.
6. Castano A, Narotsky D L, Hamid N, et al. Unveiling transthyretin cardiac amyloidosis and its predictors among elderly patients with severe aortic stenosis undergoing transcatheter aortic valve replacement. *Eur Heart J.* 2017; 38(38):2879-2887.
7. Rapezzi C, Lorenzini M, Longhi S, et al. Cardiac amyloidosis: the great pretender. *Heart Fail Rev.* 2015; 20(2): 117-124.
8. Rapezzi C, Merlini G, Quarta C C, et al. Systemic cardiac amyloidoses: disease profiles and clinical courses of the 3 main types. *Circulation.* 2009; 120(13):1203-1212.
9. Nakagawa M, Sekijima Y, Tojo K, Ikeda S. High prevalence of ATTR amyloidosis in endomyocardial biopsy-proven cardiac amyloidosis patients. *Amyloid.* 2013; 20(2):138-140.
10. Maleszewski J J. Cardiac amyloidosis: pathology, nomenclature, and typing. *Cardiovasc Pathol.* 2015; 24(6): 343-350.
11. Gertz M, Dispenzieri A, Sher T. Pathophysiology and treatment of cardiac amyloidosis. *Nat Rev Cardiol.* 2015; 12(2):91-102.
12. Narotsky D L, Castano A, Weinsaft J W, Bokhari S, Maurer M S. Wild-Type Transthyretin Cardiac Amyloidosis: Novel Insights From Advanced Imaging. *Can J Cardiol.* 2016; 32(9):1166 e1161-1166 e1110.
13. Gertz M A, Benson M D, Dyck P J, et al. Diagnosis, Prognosis, and Therapy of Transthyretin Amyloidosis. *J Am Coll Cardiol.* 2015; 66(21):2451-2466.
14. Siddiqi O K, Ruberg F L. Cardiac amyloidosis: An update on pathophysiology, diagnosis, and treatment. *Trends Cardiovasc Med.* 2018; 28(1):10-21.
15. Mollee P, Renaut P, Gottlieb D, Goodman H. How to diagnose amyloidosis. *Intern Med J.* 2014; 44(1):7-17.
16. Vrana J A, Gamez J D, Madden B J, Theis J D, Bergen H R, 3rd, Dogan A. Classification of amyloidosis by laser microdissection and mass spectrometry-based proteomic analysis in clinical biopsy specimens. *Blood.* 2009; 114 (24):4957-4959.
17. Paueksakon P, Fogo A B, Sethi S. Leukocyte chemotactic factor 2 amyloidosis cannot be reliably diagnosed by immunohistochemical staining. *Hum Pathol.* 2014; 45(7): 1445-1450.
18. Yilmaz A, Kindermann I, Kindermann M, et al. Comparative evaluation of left and right ventricular endomyocardial biopsy: differences in complication rate and diagnostic performance. *Circulation.* 2010; 122(9):900-909.
19. Cooper L T, Baughman K L, Feldman A M, et al. The role of endomyocardial biopsy in the management of cardiovascular disease: a scientific statement from the American Heart Association, the American College of Cardiology, and the European Society of Cardiology. Endorsed by the Heart Failure Society of America and the Heart Failure Association of the European Society of Cardiology. *J Am Coll Cardiol.* 2007; 50(19):1914-1931.
20. Dungu J N, Valencia O, Pinney J H, et al. CMR-based differentiation of AL and ATTR cardiac amyloidosis. *JACC Cardiovasc Imaging.* 2014; 7(2):133-142.
21. Fontana M, Pica S, Reant P, et al. Prognostic Value of Late Gadolinium Enhancement Cardiovascular Magnetic Resonance in Cardiac Amyloidosis. *Circulation.* 2015; 132(16):1570-1579.
22. Di Bella G, Pizzino F, Minutoli F, et al. The mosaic of the cardiac amyloidosis diagnosis: role of imaging in subtypes and stages of the disease. *Eur Heart J Cardiovasc Imaging.* 2014; 15(12):1307-1315.
23. Cheng Z, Kang L, Tian Z, et al. Utility of combined indexes of electrocardiography and echocardiography in the diagnosis of biopsy proven primary cardiac amyloidosis. *Ann Noninvasive Electrocardiol.* 2011; 16(1):25-29.
24. Koyama J, Ikeda S, Ikeda U. Echocardiographic assessment of the cardiac amyloidoses. *Circ J.* 2015; 79(4):721-734.
25. Quarta C C, Falk R H. Longitudinal strain imaging in light-chain cardiac amyloidosis: can it help to refine the approach to treatment? *J Am Coll Cardiol.* 2012; 60(12): 1077-1078.
26. Ahmad M M, Basraon J, Razzaque I, Port S C, Ammar K A. The complementary nature of tissue Doppler to (99m)Tc-PYP imaging in diagnosis of right ventricular cardiac amyloidosis. *J Nucl Cardiol.* 2017.
27. Dharmarajan K, Maurer M S. Transthyretin cardiac amyloidoses in older North Americans. *J Am Geriatr Soc.* 2012; 60(4):765-774.
28. Eriksson P, Backman C, Bjerle P, Eriksson A, Holm S, Olofsson B O. Non-invasive assessment of the presence and severity of cardiac amyloidosis. A study in familial amyloidosis with polyneuropathy by cross sectional echocardiography and technetium-99m pyrophosphate scintigraphy. *Br Heart J.* 1984; 52(3):321-326.
29. Lee V W, Caldarone A G, Falk R H, Rubinow A, Cohen A S. Amyloidosis of heart and liver: comparison of Tc-99m pyrophosphate and Tc-99m methylene diphosphonate for detection. *Radiology.* 1983; 148(1):239-242.
30. Falk R H, Lee V W, Rubinow A, Hood W B, Jr., Cohen A S. Sensitivity of technetium-99m-pyrophosphate scintigraphy in diagnosing cardiac amyloidosis. *Am J Cardiol.* 1983; 51(5):826-830.
31. Bokhari S, Castano A, Pozniakoff T, Deslisle S, Latif F, Maurer M S. (99m)Tc-pyrophosphate scintigraphy for differentiating light-chain cardiac amyloidosis from the transthyretin-related familial and senile cardiac amyloidoses. *Circ Cardiovasc Imaging.* 2013; 6(2):195-201.
32. Castano A, Haq M, Narotsky D L, et al. Multicenter Study of Planar Technetium 99m Pyrophosphate Cardiac Imaging: Predicting Survival for Patients With ATTR Cardiac Amyloidosis. *JAMA Cardiol.* 2016; 1(8):880-889.
33. Rapezzi C, Quarta C C, Guidalotti P L, et al. Usefulness and limitations of 99mTc-3,3-diphosphono-1,2-propanodicarboxylic acid scintigraphy in the aetiological diagnosis of amyloidotic cardiomyopathy. *Eur J Nucl Med Mol Imaging.* 2011; 38(3):470-478.
34. Rapezzi C, Quarta C C, Guidalotti P L, et al. Role of (99m)Tc-DPD scintigraphy in diagnosis and prognosis of hereditary transthyretin-related cardiac amyloidosis. *JACC Cardiovasc Imaging.* 2011; 4(6):659-670.

35. Chang I C Y, Bois J P, Bois M C, Maleszewski J J, Johnson G B, Grogan M. Hydroxychloroquine-Mediated Cardiotoxicity With a False-Positive (99m)Technetium-Labeled Pyrophosphate Scan for Transthyretin-Related Cardiac Amyloidosis. *Circ Cardiovasc Imaging.* 2018; 11(1).

36. Pomerance A, Slavin G, McWatt J. Experience with the sodium sulphate-Alcian Blue stain for amyloid in cardiac pathology. *J Clin Pathol.* 1976; 29(1):22-26.

37. Hutt D F, Quigley A M, Page J, et al. Utility and limitations of 3,3-diphosphono-1,2-propanodicarboxylic acid scintigraphy in systemic amyloidosis. *Eur Heart J Cardiovasc Imaging.* 2014; 15(11):1289-1298.

38. Sperry B W, Gonzalez M H, Brunken R, Cerqueira M D, Hanna M, Jaber W A. Non-cardiac uptake of technetium-99m pyrophosphate in transthyretin cardiac amyloidosis. *J Nucl Cardiol.* 2018.

39. Moore P T, Burrage M K, Mackenzie E, Law W P, Korczyk D, Mollee P. The Utility of (99m)Tc-DPD Scintigraphy in the Diagnosis of Cardiac Amyloidosis: An Australian Experience. *Heart Lung Circ.* 2017; 26(11):1183-1190.

40. Perugini E, Guidalotti P L, Salvi F, et al. Noninvasive etiologic diagnosis of cardiac amyloidosis using 99mTc-3,3-diphosphono-1,2-propanodicarboxylic acid scintigraphy. *J Am Coll Cardiol.* 2005; 46(6):1076-1084.

41. Yamamoto Y, Onoguchi M, Haramoto M, et al. Novel method for quantitative evaluation of cardiac amyloidosis using (201)TlCl and (99m)Tc-PYP SPECT. *Ann Nucl Med.* 2012; 26(8):634-643.

42. Kakhki V D, Zakavi S R. Age-related normal variants of sternal uptake on bone scintigraphy. *Clin Nucl Med.* 2006; 31(2):63-67.

43. Tamaki S, Kadota K, Kambara H, et al. Emission computed tomography with technetium-99m pyrophosphate for delineating location and size of acute myocardial infarction in man. *Br Heart J.* 1984; 52(1):30-37.

44. Van Der Gucht A, Cottereau A S, Abulizi M, et al. Apical sparing pattern of left ventricular myocardial (99m)Tc-HMDP uptake in patients with transthyretin cardiac amyloidosis. *J Nucl Cardiol.* 2017.

45. Kollikowski A M, Kahles F, Kintsler S, et al. In vivo quantification of amyloid burden in TTR-related cardiac amyloidosis. *Intractable Rare Dis Res.* 2017; 6(4):291-294.

46. Gillmore J D, Maurer M S, Falk R H, et al. Nonbiopsy Diagnosis of Cardiac Transthyretin Amyloidosis. *Circulation.* 2016; 133(24):2404-2412.

47. Maleszewski J J, Murray D L, Dispenzieri A, et al. Relationship between monoclonal gammopathy and cardiac amyloid type. *Cardiovasc Pathol.* 2013; 22(3):189-194.

48. Pinney J H, Whelan C J, Petrie A, et al. Senile systemic amyloidosis: clinical features at presentation and outcome. *J Am Heart Assoc.* 2013; 2(2):e000098.

49. Wiltshire J P, Custer T. Lumbar muscle rhabdomyolysis as a cause of acute renal failure after Roux-en-Y gastric bypass. *Obes Surg.* 2003; 13(2):306-313.

50. Dewanjee M K, Kahn P C. Mechanism of localization of 99mTc-labeled pyrophosphate and tetracycline in infarcted myocardium. *J Nucl Med.* 1976; 17(7):639-646.

51. Chen W, Dilsizian V. Molecular imaging of amyloidosis: will the heart be the next target after the brain? *Curr Cardiol Rep.* 2012; 14(2):226-233.

52. Pepys M B, Dyck R F, de Beer F C, Skinner M, Cohen A S. Binding of serum amyloid P-component (SAP) by amyloid fibrils. *Clin Exp Immunol.* 1979; 38(2):284-293.

53. Stats M A, Stone J R. Varying levels of small microcalcifications and macrophages in ATTR and AL cardiac amyloidosis: implications for utilizing nuclear medicine studies to subtype amyloidosis. *Cardiovasc Pathol.* 2016; 25(5):413-417.

54. Cappelli F, Gallini C, Di Mario C, et al. Accuracy of 99mTc-Hydroxymethylene diphosphonate scintigraphy for diagnosis of transthyretin cardiac amyloidosis. *J Nucl Cardiol.* 2017.

55. Osborne D R, Acuff S N, Stuckey A, Wall J S. A Routine PET/CT Protocol with Streamlined Calculations for Assessing Cardiac Amyloidosis Using (18)F-Florbetapir. *Front Cardiovasc Med.* 2015; 2:23.

56. Garcia-Gonzalez P, Cozar-Santiago M D P, Maceira A M. Cardiac Amyloidosis Detected Using (18)F-florbetapir PET/CT. *Rev Esp Cardiol (Engl Ed).* 2016; 69(12):1215.

57. Lee S P, Lee E S, Choi H, et al. 11C-Pittsburgh B PET imaging in cardiac amyloidosis. *JACC Cardiovasc Imaging.* 2015; 8(1):50-59.

58. Trivieri M G, Dweck M R, Abgral R, et al. (18)F-Sodium Fluoride PET/MR for the Assessment of Cardiac Amyloidosis. *J Am Coll Cardiol.* 2016; 68(24):2712-2714.

59. Quarta C C, Obici L, Guidalotti P L, et al. High 99mTc-DPD myocardial uptake in a patient with apolipoprotein AI-related amyloidotic cardiomyopathy. *Amyloid.* 2013; 20(1):48-51.

60. Takezaki M, Ishida Y, Morozumi T, et al. [Noninvasive diagnosis of cardiac involvement by technetium-99m-pyrophosphate (Tc-99m PYP) myocardial scintigraphy in 2 cases of familial amyloid polyneuropathy and 1 case of secondary amyloidosis]. *Kaku Igaku.* 1989; 26(12):1537-1543.

61. Harb S C, Haq M, Flood K, et al. National patterns in imaging utilization for diagnosis of cardiac amyloidosis: A focus on Tc99m-pyrophosphate scintigraphy. *J Nucl Cardiol.* 2017; 24(3):1094-1097.

62. Selvanayagam J B, Hawkins P N, Paul B, Myerson S G, Neubauer S. Evaluation and management of the cardiac amyloidosis. *J Am Coll Cardiol.* 2007; 50(22):2101-2110.

63. Murtagh B, Hammill SC, Gertz M A, Kyle R A, Tajik A J, Grogan M. Electrocardiographic findings in primary systemic amyloidosis and biopsy-proven cardiac involvement. *Am J Cardiol.* 2005; 95(4):535-537.

The citation of any document or reference is not to be construed as an admission that it is prior art with respect to the present invention.

We claim:

1. A method for diagnosing transthyretin cardiac amyloidosis in a subject, the method comprising:
   introducing a technetium-99m pyrophosphate radiotracer into a subject;
   acquiring single-photon emission computed tomography (SPECT) image data of a cardiac region of the subject based on the uptake of the radiotracer;
   acquiring anatomical image data of the cardiac region of the subject;
   combining the SPECT image data and the anatomical image data to produce a combined three-dimensional image of the cardiac region; and
   comparing the radiotracer uptake present within a first volume of interest and a second volume of interest, wherein both volumes of interest are located within the combined image of the cardiac region.

2. The method of claim 1, wherein the first volume of interest is representative of the left ventricle of the subject.

3. The method of claim 1, wherein the second volume of interest is representative of the blood pool of the subject.

4. The method of claim 3, wherein the second volume of interest is located within the right atrium of the subject.

5. The method of claim 1, wherein an average of the radiotracer uptake present within each volume of interest is used for comparison.

6. The method of claim 5, wherein a magnitude of a ratio of the radiotracer uptake in the first volume of interest to that of the second volume of interest is used to make a diagnosis.

7. The method of claim 1, wherein the anatomical image data is acquired using a computed tomography (CT) system.

8. The method of claim 7, wherein the SPECT image data and the anatomical image data are both acquired using a SPECT-CT hybrid system.

9. The method of claim 1, wherein the step of acquiring SPECT image data occurs more than 90 minutes after the step of introducing the radiotracer.

10. The method of claim 9, wherein the step of acquiring SPECT image data occurs about 3 hours after the step of introducing the radiotracer.

11. The method of claim 1, wherein regions containing calcifications within the first and second volumes of interest are excluded when comparing the radiotracer uptake.

12. A method for diagnosing transthyretin cardiac amyloidosis in a subject, the method comprising:
 introducing a radiotracer into a subject;
 acquiring single-photon emission computed tomography (SPECT) image data of a cardiac region of the subject based on the uptake of the radiotracer;
 acquiring anatomical image data of the cardiac region of the subject;
 combining the SPECT image data and the anatomical image data to produce a combined three-dimensional image of the cardiac region; and
 comparing the radiotracer uptake present within a first volume of interest and a second volume of interest, wherein the first volume of interest is representative of the left ventricle of the subject and the second volume of interest is representative of the blood pool of the subject.

13. The method of claim 12, wherein the radiotracer comprises a radioisotope selected from the group consisting of $^{99m}Tc$, $^{123}I$, $^{111}In$, $^{67}Ga$, $^{177}Lu$, $^{201}Ti$, $^{117m}Sn$, and $^{125}I$.

14. The method of claim 12, wherein the radiotracer is selected from the group consisting of technetium-99m methylene diphosphonate, technetium-99m 2,3-dicarboxypropane-1,1-diphosphonate, technetium-99m ethane-1-hydroxy-1,1-diphosphonate, and technetium-99m pyrophosphate.

15. The method of claim 14, wherein the radiotracer is technetium-99m pyrophosphate.

16. The method of claim 12, wherein the second volume of interest is located within the right atrium of the subject.

17. The method of claim 12, wherein the average of the radiotracer uptake present within each volume of interest is used for comparison.

18. The method of claim 17, wherein a magnitude of a ratio of the radiotracer uptake in the first volume of interest to that of the second volume of interest is used to make a diagnosis.

19. The method of claim 12, wherein the anatomical image data is acquired using a computed tomography (CT) system.

20. The method of claim 19, wherein the SPECT image data and the anatomical image data are both acquired using a SPECT-CT hybrid system.

21. The method of claim 12, wherein the step of acquiring SPECT image data occurs more than 90 minutes after the step of introducing the radiotracer.

22. The method of claim 21, wherein the step of acquiring SPECT image data occurs about 3 hours after the step of introducing the radiotracer.

23. The method of claim 12, wherein regions containing calcifications within the first and second volumes of interest are excluded when comparing the radiotracer uptake.

24. A system for diagnosing transthyretin cardiac amyloidosis in a subject, the system comprising:
 a source of technetium-99m pyrophosphate radiotracer;
 means for introducing the radiotracer into a subject;
 a single-photon emission computed tomography (SPECT) system configured to acquire SPECT image data of a cardiac region of the subject based on the uptake of the radiotracer;
 an imaging system configured to acquire anatomical image data of the cardiac region of the subject; and
 a processor configured to combine the SPECT image data and the anatomical image data to produce a combined three-dimensional image of the cardiac region and compare the radiotracer uptake present within a first volume of interest and a second volume of interest, wherein both volumes of interest are located within the combined image of the cardiac region.

25. The system of claim 24, further comprising a display configured to present the combined image of the cardiac region to a user.

26. The system of claim 25, wherein the user selects the location of the first and second volumes of interest within the cardiac region.

27. The system of claim 24, wherein the first volume of interest is representative of the left ventricle of the subject.

28. The system of claim 24, wherein the second volume of interest is representative of the blood pool of the subject.

29. The system of claim 28, wherein the second volume of interest is located within the right atrium of the subject.

30. The system of claim 24, wherein an average of the radiotracer uptake present within each volume of interest is used for comparison.

31. The system of claim 24, wherein a magnitude of a ratio of the radiotracer uptake in the first volume of interest to that of the second volume of interest is used to make a diagnosis.

32. The system of claim 24, wherein the imaging system is a computed tomography (CT) system.

33. The system of claim 32, wherein the SPECT image data and the anatomical image data are both acquired using a SPECT-CT hybrid system.

34. The system of claim 24, wherein regions containing calcifications within the first and second volumes of interest are excluded when comparing the radiotracer uptake.

* * * * *